United States Patent
Rivas et al.

(10) Patent No.: US 10,429,389 B2
(45) Date of Patent: Oct. 1, 2019

(54) METHOD FOR IDENTIFYING ALTERED LEUKOCYTE PROFILES

(71) Applicants: Ariel L. Rivas, Albuquerque, NM (US); Gabriel Leitner, Mazkeret Batya (IL); Almira L. Hoogesteyn, Merida (MX)

(72) Inventors: Ariel L. Rivas, Albuquerque, NM (US); Gabriel Leitner, Mazkeret Batya (IL); Almira L. Hoogesteyn, Merida (MX)

( * ) Notice: Subject to any disclaimer, the term of this patent is extended or adjusted under 35 U.S.C. 154(b) by 724 days.

(21) Appl. No.: 14/769,030

(22) PCT Filed: Feb. 19, 2014

(86) PCT No.: PCT/US2014/017181
§ 371 (c)(1),
(2) Date: Aug. 19, 2015

(87) PCT Pub. No.: WO2014/130564
PCT Pub. Date: Aug. 28, 2014

(65) Prior Publication Data
US 2016/0003821 A1    Jan. 7, 2016

Related U.S. Application Data

(60) Provisional application No. 61/766,589, filed on Feb. 19, 2013.

(51) Int. Cl.
*G01N 33/569* (2006.01)
*G16H 50/70* (2018.01)
*G06F 19/00* (2018.01)

(52) U.S. Cl.
CPC ....... *G01N 33/56972* (2013.01); *G06F 19/00* (2013.01); *G16H 50/70* (2018.01); *Y02A 90/26* (2018.01)

(58) Field of Classification Search
None
See application file for complete search history.

(56) References Cited

U.S. PATENT DOCUMENTS

| 2004/0225449 A1 | 11/2004 | Bevilacqua et al. |
| 2007/0038384 A1 | 2/2007 | Kirk et al. |
| 2009/0163228 A1 | 6/2009 | Blumberg et al. |
| 2009/0319191 A1 | 12/2009 | Rivas et al. |

OTHER PUBLICATIONS

Rivas et al., Feedback-Based, System-Level Properties of Vertebrate-Microbial Interactions, PLOS One, vol. 8, No. 2, p. e53984. Feb. 20, 2013.
Adjouadi et al., Classification of Leukemia Blood Samples Using Neural Networks, Annals of Biomedical Engineering, vol. 38, No. 4, pp. 1473-1482. Dec. 15, 2009.

*Primary Examiner* — G Steven Vanni
(74) *Attorney, Agent, or Firm* — Hodgson Russ LLP

(57) ABSTRACT

Methods of identifying altered leukocyte profiles are disclosed. In one embodiment, counts or relative percentages of leukocyte cell types are received and constitute input data points. Combinations of input data points are generated. Pairs of input data points and combinations are generated. Secondary data values are generated from the pairs. Three-dimensional plots are then constructed and selected as useful for identifying an altered leukocyte profile through pattern recognition of perpendicular data inflection, data bifurcation, non-overlapping data clusters, or combinations thereof. Such a strategy results in partially or totally non-overlapping data subsets, which are then interpreted.

18 Claims, 28 Drawing Sheets

| Patient ID # | Discrete or discontinuous ['yes/no'-like] input data | Continuous (e.g., relative leukocyte percentage) input data | | |
|---|---|---|---|---|
| | | L % (A) | PMN or N (B) % | M % (C) |
| 1 | No or negative (non-inflamed/non-infected) | 60 | 15 | 15 |
| 2 | Yes or positive (inflamed/infected) | 25 | 60 | 15 |
| 3 | Yes | 20 | 70 | 10 |
| 4 | No | 63 | 12 | 15 |

| ID | Discrete data | Continuous data | | | Secondary continuous data, derived from input data | | | | | | | | | | |
|---|---|---|---|---|---|---|---|---|---|---|---|---|---|---|---|
| | | A | B | C | D | E | F | G | H | I | J | K | L | M | ... | $n^{th}$ |
| 1 | No | 60 | 15 | 15 | xx | xx | xx | xx | xx | xx | xx | xx | xx | xx | ... | xx |
| 2 | Yes | 25 | 60 | 15 | xx | xx | xx | xx | xx | xx | xx | xx | xx | xx | ... | xx |
| 3 | Yes | 20 | 70 | 10 | xx | xx | xx | xx | xx | xx | xx | xx | xx | xx | ... | xx |
| 4 | No | 63 | 12 | 15 | xx | xx | xx | xx | xx | xx | xx | xx | xx | xx | ... | xx |

Fig. 7

METHOD FOR IDENTIFYING ALTERED LEUKOCYTE PROFILES

CROSS-REFERENCE TO RELATED APPLICATIONS

This application claims priority to U.S. Provisional Application No. 61/766,589, filed on Feb. 19, 2013, now pending, the disclosure of which is incorporated herein by reference.

FIELD OF THE INVENTION

The invention relates to methods for identifying altered leukocyte profiles for evaluating health status and monitoring diseases.

BACKGROUND OF THE INVENTION

Infectious disease is the result of actions and counteractions performed by an infecting pathogen, the immune system, or both. Because such actions occur over time, and both the microbe and the immune system may differ in many aspects, different outcomes may occur over time, i.e., immuno-microbial interactions are not static or constant.

The present invention addresses several problems and needs described in the medical literature—some of these problems and needs known for more than 30 years. One such problem is the 'cost of dichotomization.' The cost of dichotomization is an error-prone method. (Cohen J., THE COST OF DICHOTOMIZATION. *Applied Psychological Measurement* 7: 249; 1983). When a continuous variable (such as the relative percentage of a cell type) is divided into two subsets (dichotomized) and the data subsets above or below a cut-off value receive non-continuous (discrete) labels (such as 'yes/no', 'negative'/'positive', or 'non-inflamed'/'inflamed'), a substantial number of (false-negative, false-positive) errors are generated. For example, numerous true 'negative' observations will be found within the data range of 'positives' (false positives) and vice versa—numerous true 'positive' data points will be located within the data range of 'negatives' (false negatives).

The cost of dichotomization problem is shown in FIGS. 1A-D. The relative percentage of three cell types (lymphocytes [L], polymorphonuclear cell or neutrophil [PMN or N], and macrophage/monocyte [M]) failed to distinguish non-infected from infected individuals. Instead, overlapping leukocyte values were observed (rectangles, FIG. 1A). This means that any cut-off value of any of the cell types considered would result in false-negatives and/or false-positives. The 'cost' associated with 'dichotomization' is also revealed by linear models: if data points from infected and non-infected individuals were assumed to be linearly distributed, the point where the two data curves cross one another could be determined (vertical line, FIG. 1B). The cut-off point determines the data range within which data points of one category predominate over observations of the other category. Indeed, most 'infected' individuals predominated above such point (at the right half of the plot) while 'non-infected' individuals predominated below such point (left half of the plot). However, because such curves do not end at such point, a large error area can be observed: out of 24 data points, at least 5 false negative (FN) and 5 false positive (FP) data points are observed (due to similar values, 4 data points are not observed—they overlap, FIG. 1C). Such errors represent a 50% (10/20) total error rate (FIG. 1C). The high cost of the dichotomization procedure (the classic or current paradigm) is not the result of a particular cell type. If, instead of PMN %, lymphocyte percentages were considered, two-digit percent errors would also be observed (FIG. 1D). Two-digit percent errors are frequently found in the prior art when a cut-off value is used. 'Dichotomization' is also costly because, in tabular or any non three-dimensional (3-D) data format, data points perpendicular to the plane of analysis are missed.

Another problem in the prior art is delayed information, where information is not available in real time. One other problem in the prior art involves information loss, such as non-interpretable data. Such data is unusable data because it lacks differentiation of different data classes.

BRIEF SUMMARY OF THE INVENTION

The present disclosure provides a method for identifying altered leukocyte profile by pattern recognition. The identified altered leukocyte profile may indicate inflammation, exposure to a pathogen, infection, or exposure to a pathogen and subsequent recovery. In one embodiment, the present method based on pattern recognition allows discrimination of false positives or negatives based on spatial contrasts between plotted data points. In one embodiment, the identified altered leukocyte profile indicates a temporal stage of an infection.

In one embodiment, the method comprises the steps of obtaining input data on leukocyte numbers and subtypes, expanding the data based on combinations of the input data, grouping and plotting of combinations of input data such that patterns are generated from which discrimination of individual inputs of test sample data may be carried out.

The leukocyte numbers (counts) and subtype relative percentages may be determined in any suitable biological sample such as a biological fluid. The biological fluid is any fluid from an individual's body comprising leukocytes—whether obtained directly from the individual or whether subjected to some process—such as cell culture—before a fluid is collected. Thus, for example, a cell culture medium comprising leukocytes is considered to be a biological fluid for this disclosure. In one embodiment, the biological fluid may be blood, peritoneal fluid, milk, nasal secretions, lavage fluids, cerebrospinal fluid, lymph, saliva, urine and the like. In one embodiment, the biological fluids may be a synthetic medium comprising leukocytes.

In one embodiment, the leukocyte cell types comprise lymphocytes (L), monocytes (M), and neutrophils (N). Monocytes include macrophages. Neutrophils include polymorphonuclear cells (PMN). In another embodiment, the leukocyte cell types may be eosinophils and basophils. Groups of such cell types may also be used—such as phagocytes (neutrophils and monocytes) (P), mononuclear cells (MC) (monocytes and neutrophils), and "small leukocytes" (SL) (lymphocytes and neutrophils). The biological fluid comprises leukocytes from at least one individual.

The various cell types can be determined by routine methods that are well known in the art. For example, leukocyte cell types can be determined through flow cytometry. Another method includes microscopic classification after applying a stain to the biological fluid.

In one embodiment, the method comprises obtaining counts or relative percentages of leukocyte subtypes. These constitute input data points. The input data points may be obtained from a plurality of individuals or from for the same individual. The input data points may be obtained at one time or over a period of time.

In one embodiment, the method comprises the step of obtaining a plurality of input data points, and then expanding the data by generating a plurality of combinations of input data points. For example, combinations of data points may include M+N or M/N—either in a plurality of individuals or in a single individual at one time, or over a period of time. The expanded data is then grouped. For example, a group may be (M/N)/(N/L). These are referred to as secondary data values. The data is then plotted. For example, a plurality of 3-D plots may be constructed from the grouped or input data points. In one embodiment, each plot uses a set of three values, wherein the values may be input data points, secondary data values, or combinations thereof. In one embodiment, the 3-D plots use at least one secondary value. The plots may have additional dimensions based on additional sets having three input data points, secondary data values, or combinations thereof. The 3-D plots may provide standard or reference plots. The 3-D plots are useful for identifying an altered leukocyte profile through pattern recognition. For examples, patterns generated in the 3-D plots may be of perpendicular data inflection, data bifurcation, non-overlapping data clusters, or combinations thereof. Pattern recognition may comprise differences in spatial location between data points, data points projected on different planes, or data points projected on different dimensions. In one embodiment, pattern recognition is prioritized in the order of triple perpendicular data inflection, single perpendicular data inflection, data bifurcation, and non-overlapping clusters.

In one embodiment, the method further comprises the steps of receiving counts or relative percentages of leukocyte cell types from a test individual, grouping and obtaining secondary data values, determining the test individual's location in the relevant leukocyte 3-D profile, and optionally determining a biological condition based on the calculated location. For example, if a 3-D plot is used in which [P/L]/[SL/M] is plotted over [MC/N]/[P/L] and [MC/N]/[SL/M], then the same secondary values, would be generated for the test sample and the secondary values then plotted on the 3-D plot.

In another embodiment, the method further comprises the step of receiving an indication associated with each individual. In such embodiments, the altered leukocyte profiles are selected based on the indications.

In one embodiment, the method further comprises the step of establishing spatial areas in the identified altered leukocyte profile corresponding to certain indications. Further embodiments are discussed herein.

The method of the present disclosure is applicable across vertebrate species and regardless of the type of pathogen (viral, bacterial, or parasite-related) involved. This method detects and distinguishes false results; provides time-related information (even when chronological data are not available), such as the sequence of disease stages (e.g., 'early' and 'late' stages); differentiates several medical conditions; and provide graphic and numerical information on functions (multi-factor interactions) even when such variables are not explicitly investigated.

The present method can obtain input data points from existing data, such as available leukocyte data. The present invention can be used to generate information that indicates whether an individual or a group of individuals experience inflammation As used herein, inflammation can be described as a biological response, such as an immune response related to infection. The biological response may indicate an infection or lack thereof.

To address the problems described above, a counter-intuitive strategy is followed. In the present method, nothing actually tested (whether "input" or "combined" data) is of consequence by itself. By recognizing patterns first, critical variables can be identified. Their values can later be extracted, even if such critical variables were not explicitly investigated. This is so because complex systems (multi-layered and dynamic biological structures that perform numerous functions with a few elements) reveal three characteristics (novelty, irreducibility, and unpredictability) which cannot be detected or predicted by simple analysis of its primary components. High-level (i.e., system-level) characteristics only emerge when the overall system is assembled. Such characteristics are not detected at a 'low-level' (e.g., the cell types that constitute such system, when measured in isolation). As such, the goal of this method is to detect 'emergence' of high-level characteristics, not to measure 'low-level' components.

'Emergent' (novel, irreducible, or unpredictable) features are found in combinatorial, multi-variable, multi-level, and dynamic processes. The more complex the structure, the greater the information generated. Emergent properties cannot be anticipated by the analysis of low-level data.

One property of 'complex systems' is 'unpredictability': measuring 'low-level' elements (such as counts or percents of separate cell types) does not explain how it works. Consequently, no equation can predict a system. However, the present invention can express 'high-level' features—which are very informative.

Biological systems, such as the immune system, are highly complex. For example, the immune system performs a very large number of functions with only a few elements. The immune system exhibits several important characteristics. For instance the immune system exhibits: (i) synergy—providing an 'economical' solution (more can be achieved with less, faster, at a lower cost); (ii) redundancy—preserving life when a particular or 'specialized' sub-system fails, offering alternative sub-systems which may perform the needed function—even if that is achieved at a higher cost; and (iii) pluri-potentiality—compensating the greater cost associated with redundancy and contributes to solve the problem associated with thousands (or millions) of pathogens, even when the number of available resources is very small, i.e., by facilitating a high number of combinations, most immune functions are performed by only a few (usually, three) cell types. Furthermore, temporal changes may occur in a complex system. For example, the same element may perform different—even opposite—functions, e.g., the macrophage first promotes neutrophil activity and later kills neutrophils.

The present invention reveals complex system characteristics. In one embodiment, the present invention utilizes 3D space to achieve these goals. Because three-dimensional (3D) space expresses not only the values of 3 axes but also the overall (resulting) expression of the three axes in interaction, the location of each data point, in 3D space, reflects at least two 'levels' of complexity: (i) a 'lower level of complexity' (the information contributed by each variable/axis), and (ii) a 'higher level or complexity' (that of the overall, 3D interaction). However, additional (even higher) levels of complexity may also be measured, e.g., when complex ratios are used.

In addition, the present invention possesses eight features:

1. The invention reveals reduced data variability, without eliminating data values. For example, errors associated with data variability are minimized or prevented through this feature. Data variability is eliminated from all dimensions but one—that of the single line of observations. Because any data point (by design) can only fall within a single, one-data point wide line, variability is limited to the location of points within a single line. That eliminates the need of any quantitative (statistical) analysis. To interpret such a line, only location is needed. When temporal data is available, it is relevant to determine if data points from the same individual are 'moving' toward one or the other end (directionality).

2. The invention achieves functional data integrity, i.e., it measures, simultaneously, all leukocyte cell types on which there is information, not isolated cell types (such as a single cell type). This principle promotes the detection of complex systems (i.e., to detect emergence) because all the data points on all the cell types are investigated together (not in isolation).

3. The invention measures three-dimensional functions (3D interactions). For example, the invention assesses dynamic processes (temporal changes), which involve two or more cell types (i.e., the method does not measure constant or static elements, measured in isolation). This principle prevents errors associated with data variability, because data structures are created in a way such that they may reveal a single, one data point-wide line.

4. The invention captures complexity. For example, the invention measures interactions among interactions, such as the quasi-infinite interactions that may take place in three-dimensional (3D) space. For example, the present invention simultaneously assesses 3 variables (simple, or complex), each expressed along each axis of a 3D plot. A 3D plot may reveal three levels of complexity when: (i) a simple ratio (complexity level I) is measured in one axis; (ii) at least one complex ratio (complexity level II) is measured in another axis, and (iii) the overall (3D) interaction among interactions (complexity level III) is assessed by the 3D plot.

5. The invention focuses on pattern recognition and is free of any numerical 'cut-off'-based results. For example, the interpretation is based on graphical patterns, not on any one number or variable. In this way, the invention can retrieve, after emergence is detected, not only the numerical values associated with distinct, 3D patterns, but also information on interactions not explicitly investigated.

6 and 7. The invention provides both redundancy and reproducibility. For example, the same inferences can be made when different data structures are assessed, and the same data structure may be applied to different host species affected by different pathogens/conditions.

8. The invention reveals emergence, in real-time. The invention provides new ['system-level'] information immediately upon use. For example, the method can be implemented through computer software to meet this principle.

DESCRIPTION OF THE DRAWINGS

For a fuller understanding of the nature and objects of the invention, reference should be made to the following detailed description taken in conjunction with the accompanying drawings, in which:

FIG. 7 is a chart showing data expansion by generating secondary data based on input data;

DETAILED DESCRIPTION OF THE INVENTION

Figure 1A:
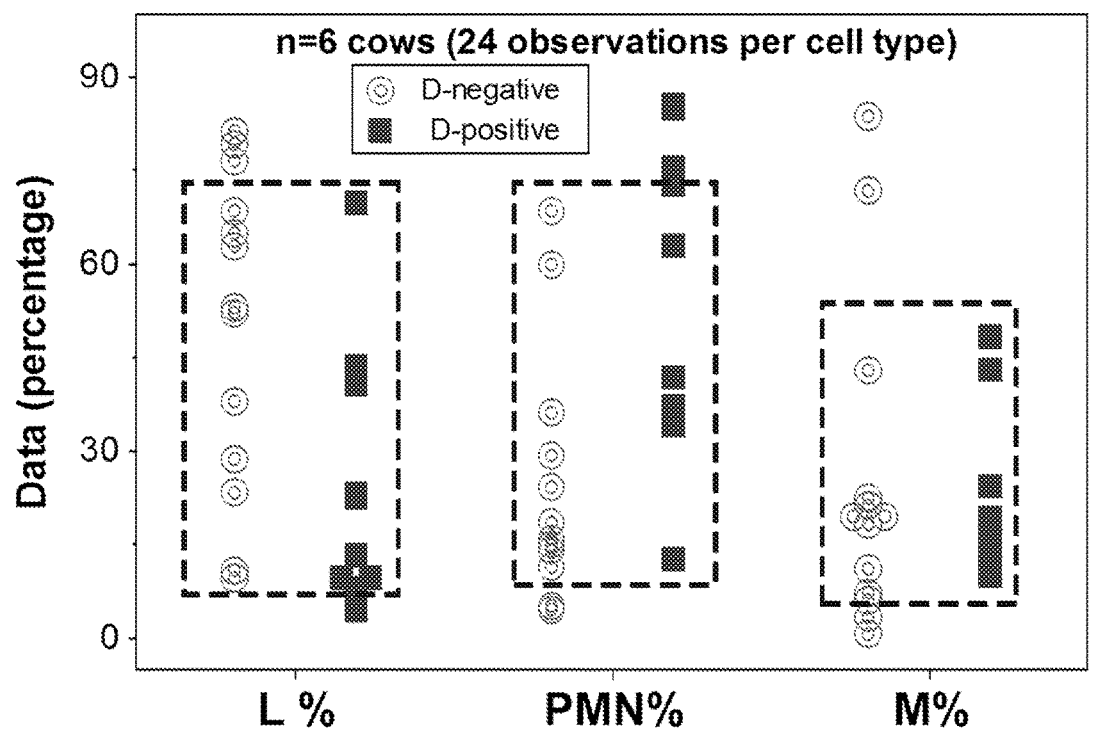
FIGS. 1A-D are graphs showing the cost of dichotomization when analyzing leukocyte data using prior methods.
Figure 1B:
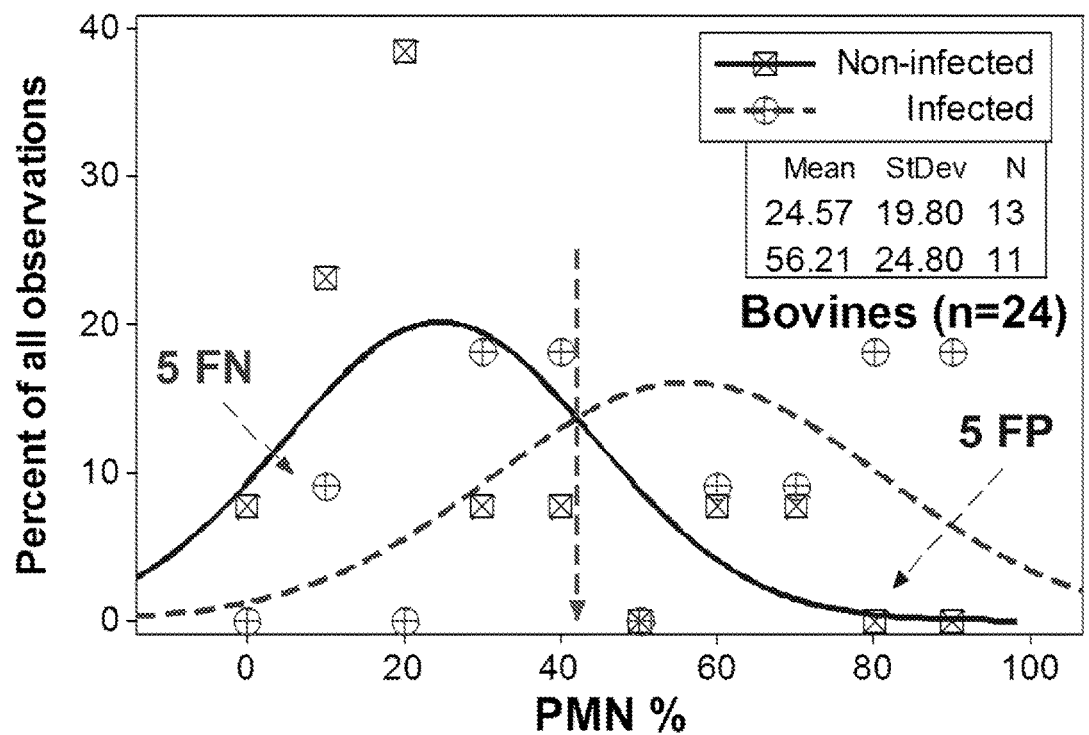
Figure 1C:
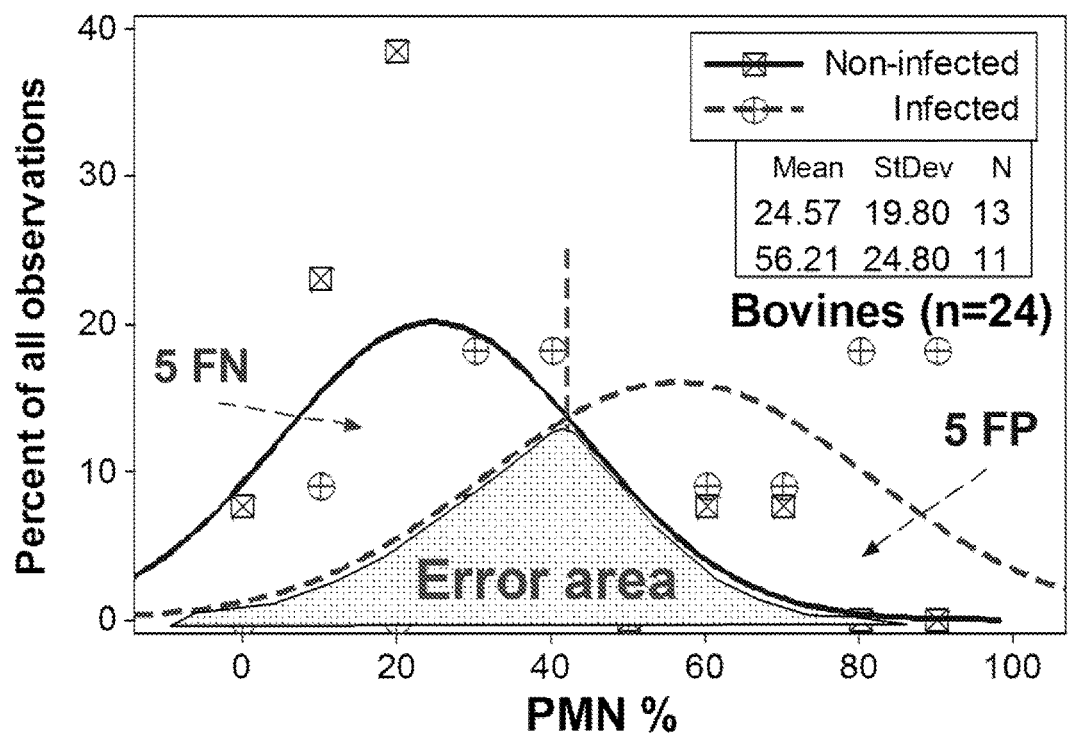
Figure 1D:
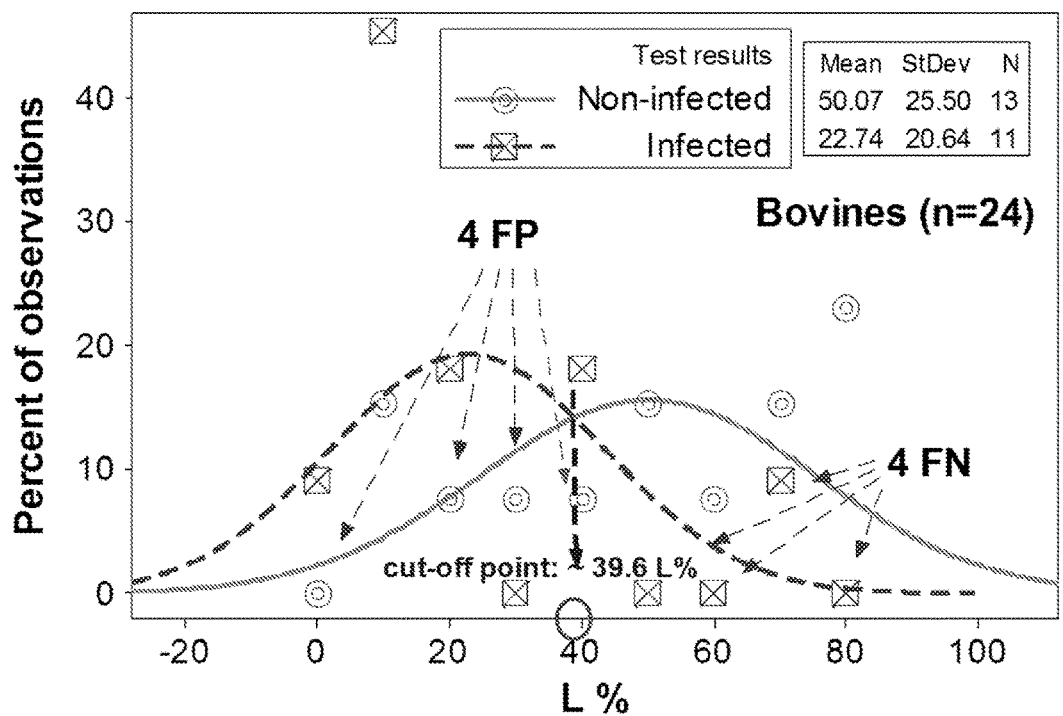

One embodiment of the present invention is a method for identifying altered leukocyte profile by pattern recognition. The identified altered leukocyte profile may indicate inflammation, exposure to a pathogen, infection, or exposure to a pathogen and subsequent recovery. In one embodiment, the identified altered leukocyte profile indicates false positives or negatives based on spatial location. In another embodiment, the identified altered leukocyte profile indicates a temporal stage of an infection, or any other altered condition.

The method comprises the step of receiving 101 counts or relative percentages of leukocyte cell types in a biological fluid. In one embodiment, the biological fluid is blood, saliva, milk, peritoneal fluid, cerebrospinal fluid, urine, or any other fluid derived from an individual's body which contains leukocytes. In one embodiment, the biological fluid is a synthetic fluid, such as a buffer, comprising leukocytes.

In one embodiment, the leukocyte cell types comprise lymphocytes (L), monocytes (M), and neutrophils (N). Monocytes include macrophages. Neutrophils include polymorphonuclear cells. These three cell types represent ~90% of all leukocytes. In other embodiments, other leukocyte cell types may also be included in the input data points. For example, other leukocyte cell types may comprise basophils, and eosinophils. In other embodiment, other subtypes or groups may also be used—such as phagocytes, macrophages and the like.

The biological fluid is from at least one individual. The counts or percentages constitute input data points. The input data points may comprise counts or relative percentages of leukocyte cell types at various times for the same individual. For example, a single individual could be tested multiple times (such as, 2, 3, 4, or 5 times). Each test would constitute a different input data point. The individual may have a known status (e.g., inflammation) or the status of the individual may be unknown. The counts or percentages may also be from a plurality of individuals obtained, which may optionally be obtained over a period of time. The data points generated can be used to generate a standard or reference plot.

The present invention does not utilize population-based (statistics-related) metrics. Thus, data from a single individual is valuable according to the present invention. As described below, distinct patterns can be recognized in these embodiments.

In one embodiment, the method comprises obtaining input data points from the counts or percentages of leukocyte subtypes and then generating 103 a plurality of combinations of input data points to provide combination data points. Each combination data point is generated from at least two leukocyte cell types. From the plurality of input data points and combination of input data points, a plurality of pairs may be generated 105. Each pair comprises two input data points, an input data point and a combination data point, or two combination data points. Each pair may also comprise more than two data points. In one embodiment, the state of the one or more individuals is irrelevant. A status of one or more individuals (e.g., inflammation) may be known. In another embodiment the individual or individuals are known to be without inflammation. In other embodiments, the status of the one or more individuals are unknown.

From the plurality of pairs, a plurality of secondary data values may be generated 107. The secondary data values comprise simple or complex ratios of input data points. For example, the secondary values may comprise a ratio of two input data points, a ratio of an input data point and a combination data point or a ratio of two combination data points.

The ratios may be simple ratios—such as ratios of two input data points, or they may be complex ratios such as a ratio of two ratios. In some embodiments, at least one of the complex ratios comprise two or more leukocyte cell types in the ratio's denominator or numerator. One example of a complex ratio is (M/N)/(N/L). In another example, leukocyte cell types further comprise phagocytes (P) and a complex ratio is [(M*L)/N]/[P/L].

After obtaining a plurality of secondary values, the method comprises the step of constructing 109 a plurality of 3-D plots. Each plot uses a set of three values—which may be input data points, secondary data values, or combinations thereof. In one embodiment, the 3-D plots use at least one secondary value. The plots may have additional dimensions based on additional sets having three input data points, secondary data values, or combinations thereof.

The method further comprises the step of selecting 111 the 3-D plots as useful for identifying an altered leukocyte profile through pattern recognition of perpendicular data inflection, data bifurcation, non-overlapping data clusters, or combinations thereof. Pattern recognition may comprise differences in spatial location between data points, contrasts (spatial or otherwise), data points projected on different planes, or data points projected on different dimensions. In one embodiment, pattern recognition is prioritized in the order of triple perpendicular data inflection, single perpendicular data inflection, data bifurcation, and non-overlapping clusters.

In one embodiment, the method further comprises the steps of receiving 113 counts or relative percentages of leukocyte cell types from a test individual, generating secondary data values, identifying 115 the test individual's location in the selected leukocyte profile, and determining 117 a biological condition based on the calculated location.

In another embodiment, the method further comprises the step of receiving an indication associated with each individual. In such embodiments, the altered leukocyte profiles are selected based on the indications.

In one embodiment, the method further comprises the step of establishing spatial areas in the identified altered leukocyte profile corresponding to certain indications. Further embodiments are discussed herein.

Exemplary Embodiments of the Invention

One embodiment of the present invention can be described as a method for expanding the number of indicators associated with animal health (including human health) monitoring and infectious (bacterial and parasite-related) diseases.

While discussing certain embodiments, the following definitions are used: (i) 'Positive': likely to be an inflammation/stress, 'infected,' or 'bacteria-positive' condition; (ii) 'Negative': likely to be 'non-inflamed', 'non-infected,' or 'bacteria-negative' condition; (iii) False negative: a bacteriologically negative test result that, in a data structure that includes negative and positive test results, is surrounded by 'positive' data points and/or is located far from where most 'negative' data points are observed; (iv) False positive: a bacteriologically positive test result that, in a data structure that includes negative and positive test results, is located in a position far from where most 'positive' data points are observed; (v) Neither exposed nor infected: individuals most likely free of disease; (vi) Previously exposed or infected, now recovered: individuals most likely under recovery, after being infected by or exposed to an infective agent; (vii) Simple ratio: the quotient generated by dividing two percentages; (viii) Double (or complex) ratio: the quotient generated by creating two simple ratios and, later, dividing the value of the numerator ratio over the value of the denominator ratio.

Figure 2A:
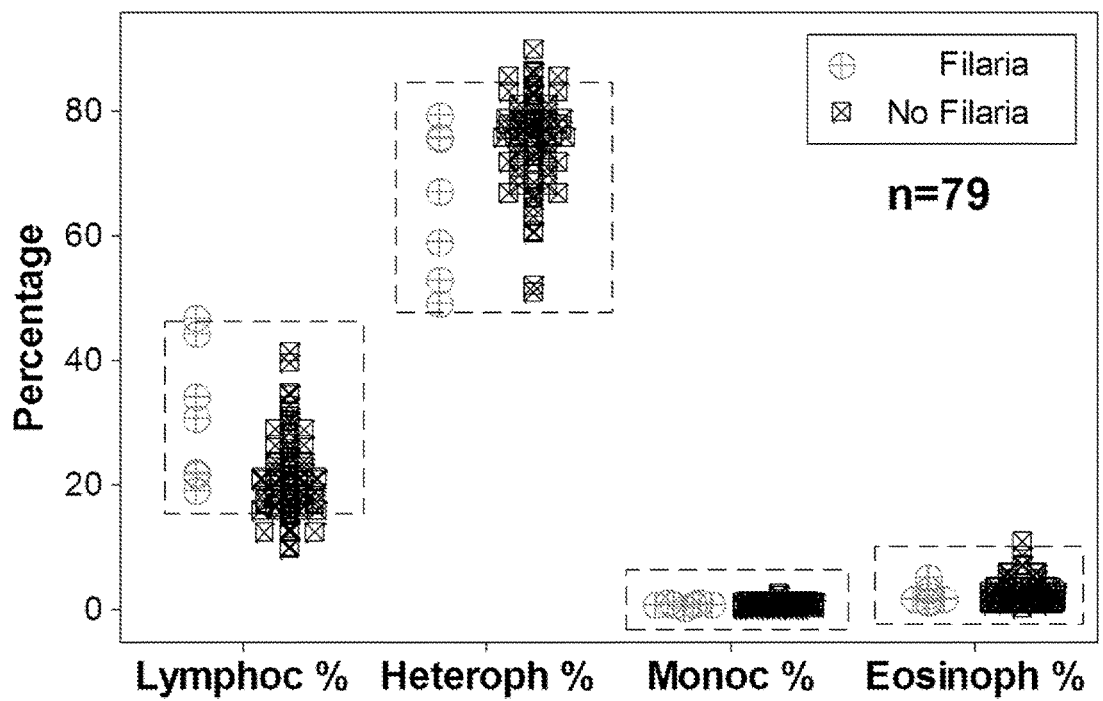
FIGS. 2A-H are graphs showing avian leukocyte data patterns collected from two wildlife species according to one embodiment of the present invention.
Figure 2B:
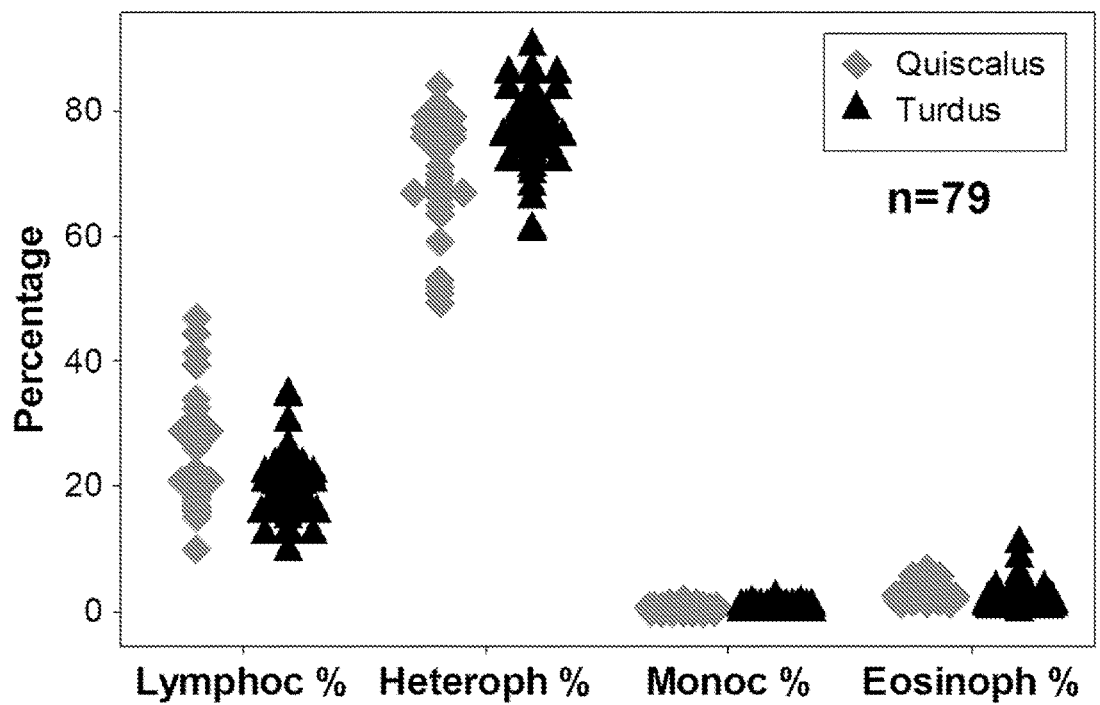
Figure 2C:
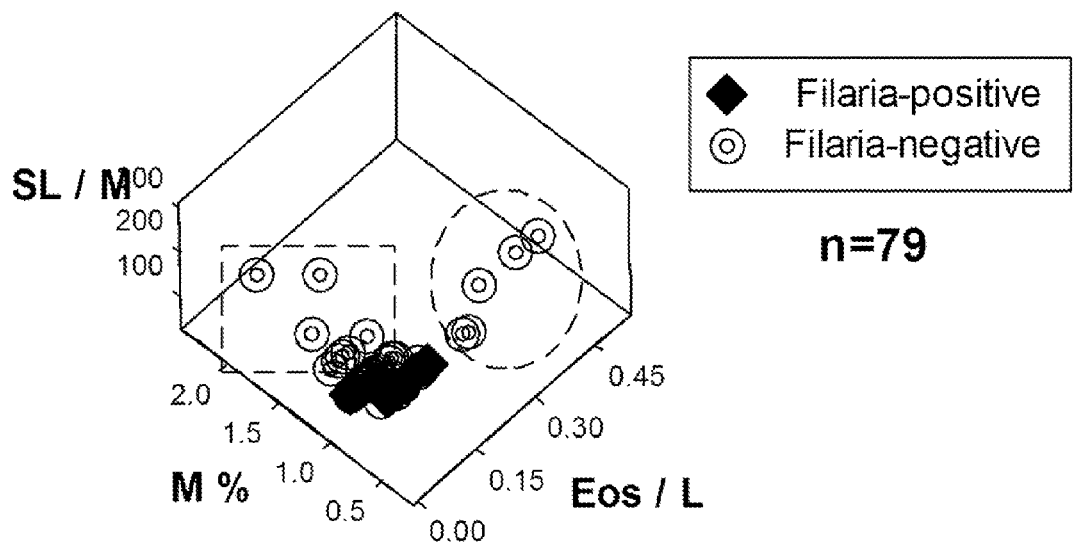
Figure 2D:
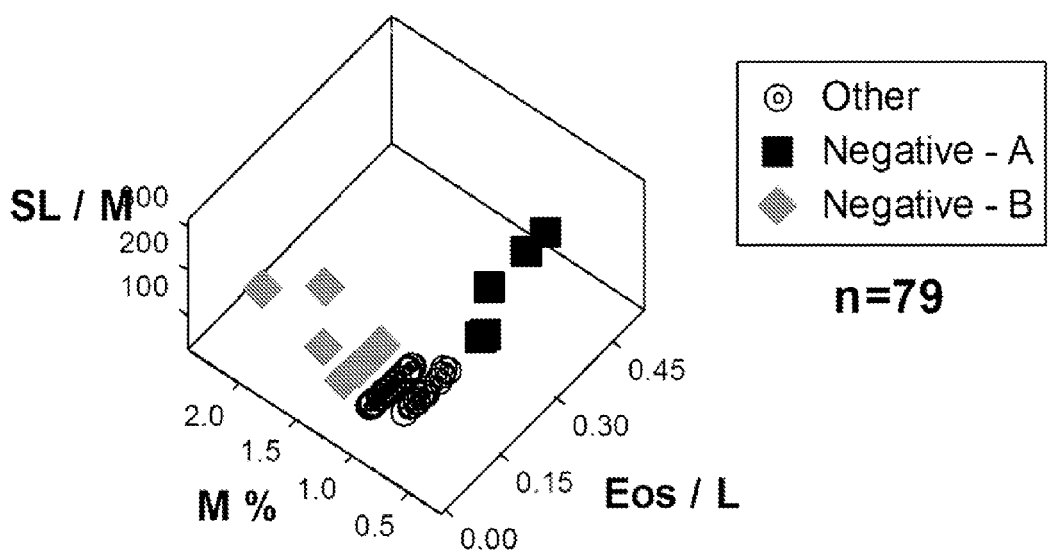
Figure 2E:
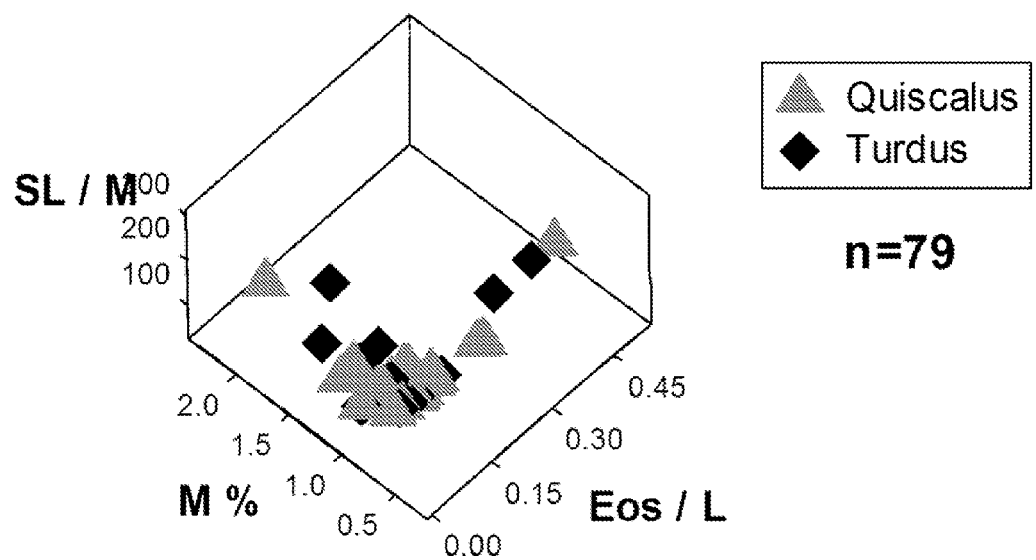
Figure 2F:
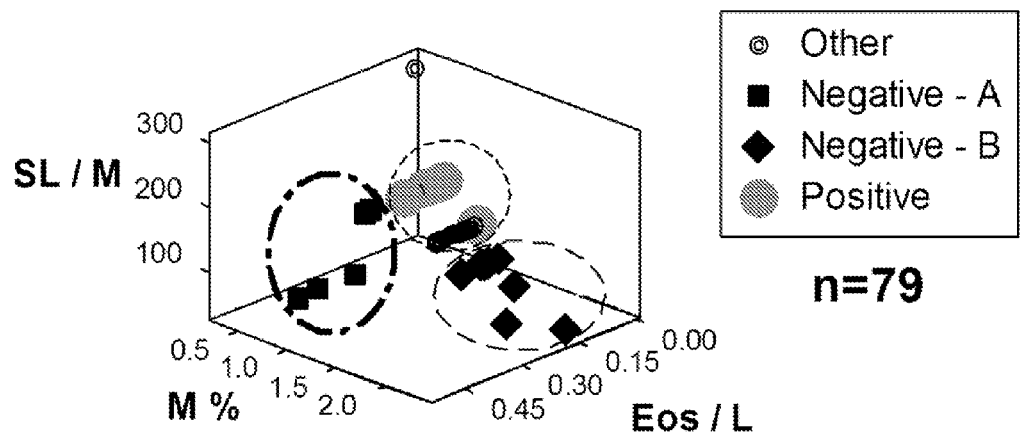
Figure 2G:
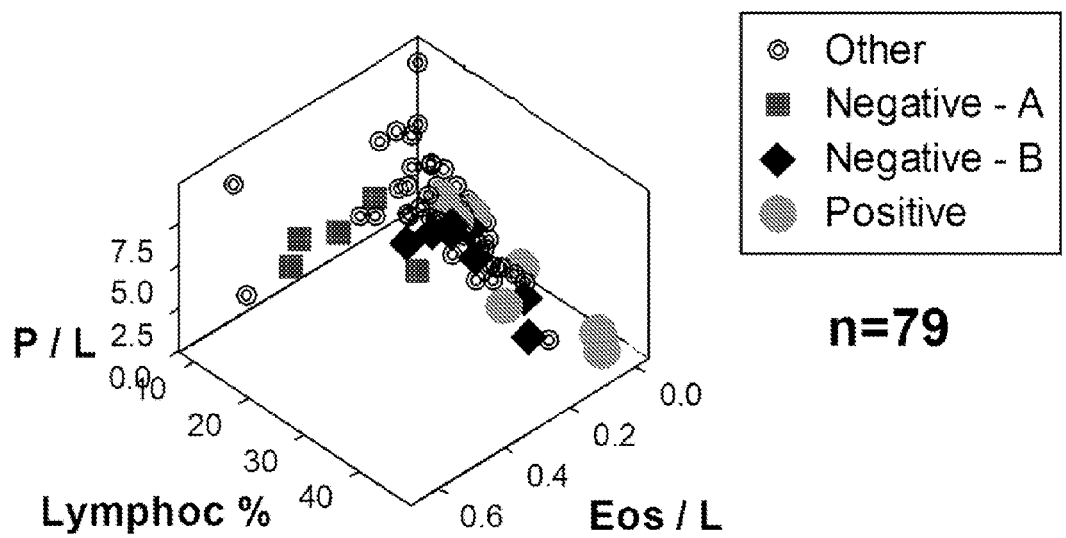
Figure 2H:
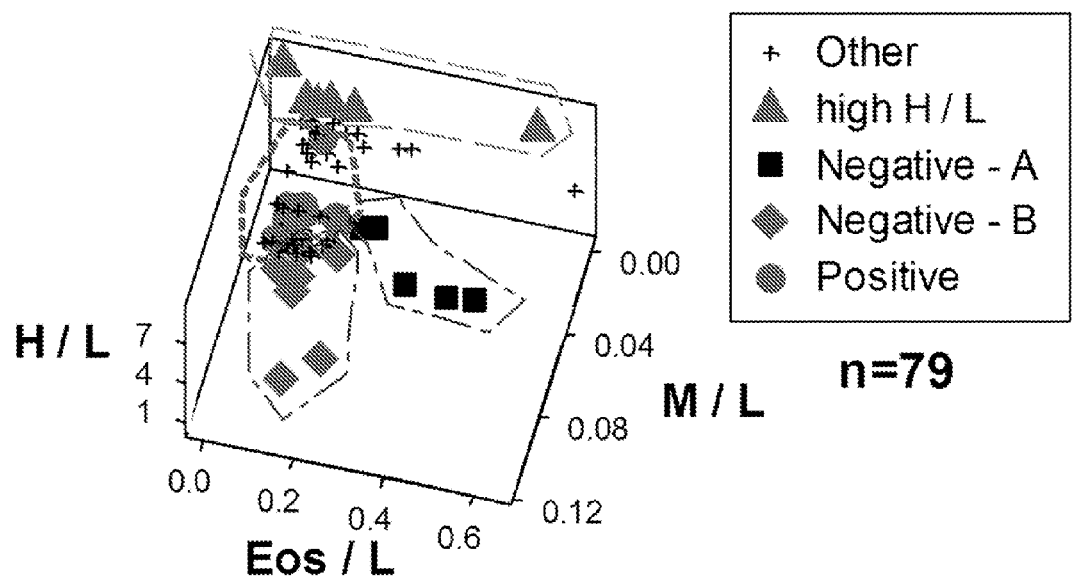

FIGS. 2A-H show avian leukocyte data patterns collected from two wildlife species (n=79), according to one embodiment of the invention. In 7 birds, micro-filaria (parasites) were detected. However, the presence of filaria is not indicative of disease; on the contrary, there are reports indicating a synergic (filarial-bird) relationship, not yet understood. When classic indicators (relative percentages) of predominant leukocyte types—such as lymphocytes—are plotted, most filaria-negative and—positive observations overlap (FIG. 2A). Such overlapping data pattern was not caused by any one species: both avian species contributed observations to each (filarial-negative, -positive) data subset (FIG. 2B). However, when leukocyte data are structured in ways such that at least one indicator is structured as a ratio (e.g., the Eos/L ratio or ratio between the eosinophil percent over the lymphocyte percent), two non-overlapping data subsets, composed of filaria-negative data points, are observed (FIG. 2C). In FIG. 2C, a perpendicular data inflection distinguishes two sets of filarial-negative observations. Such subsets are here named 'negative A' and negative B' data subsets (FIG. 2D). These 'negative' data subsets were not the effect of any one bird species: both avian species contributed to such data subsets, i.e. filarial-negative classes (FIG. 2E). Such data subsets did not overlap: when the same data are analyzed under a different perspective, it is noticed that none of the 3 (one 'positive', two 'negative') subsets overlap with one another (FIG. 2F). When other indicators also constructed as ratios are considered, the 'positive' subsets reveal a perpendicular data inflection with respect to the 'negative A' subset (FIG. 2G). Furthermore, when all the 3 indicators (one per axis) are structured as ratios, an additional data subset is distinguished (here named 'high H/L [high heterophil/lymphocyte ratio), and total discrimination (no overlapping) among the 4 subsets is observed (FIG. 2H). Therefore, the way the leukocyte data are structured determines whether no discrimination (FIG. 2A) or discrimination (FIGS. 2F-H) is generated.

Figure 3A:
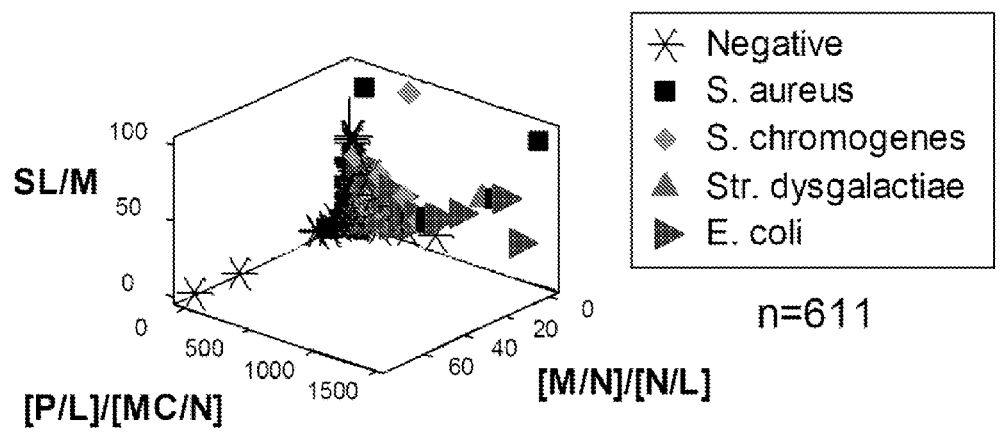
FIGS. 3A-H are graphs showing bovine leukocyte data collected from two studies (one cross-sectional and non-experimental [n=611], and one longitudinal and experimental [n=6 cows, measured 4 times each, or 24 observations]) according to one embodiment of the present invention.
Figure 3B:
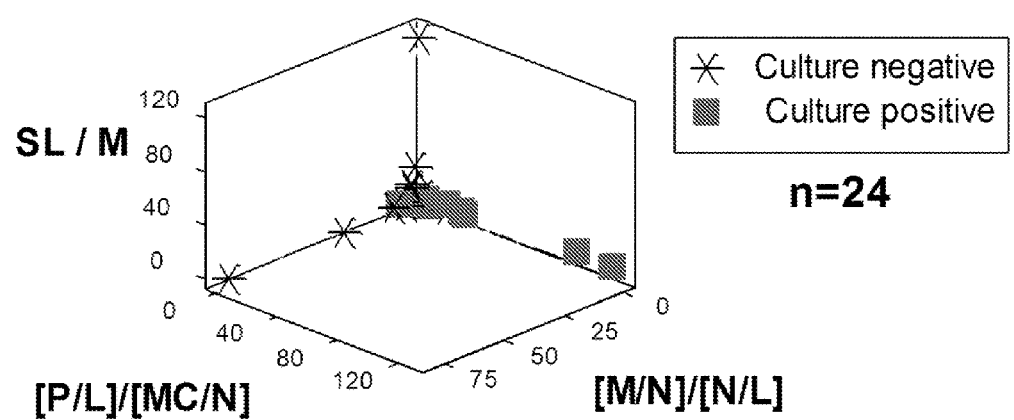
Figure 3C:
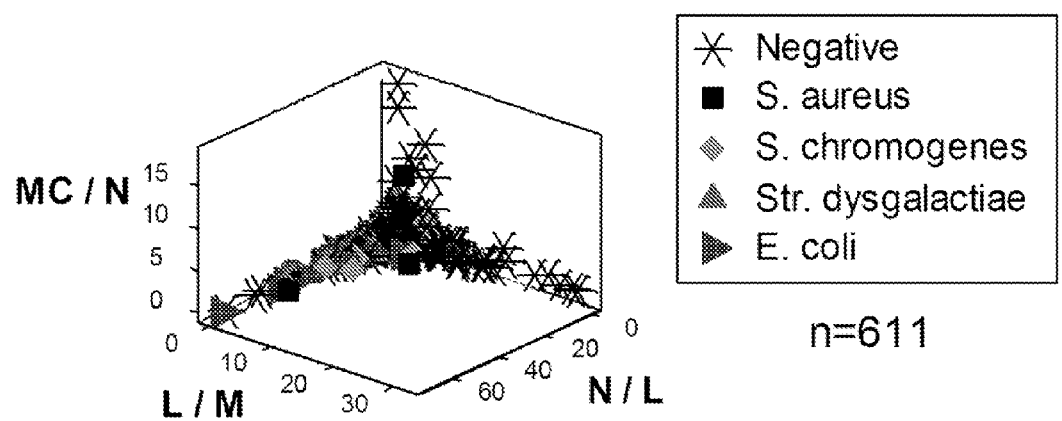
Figure 3D:
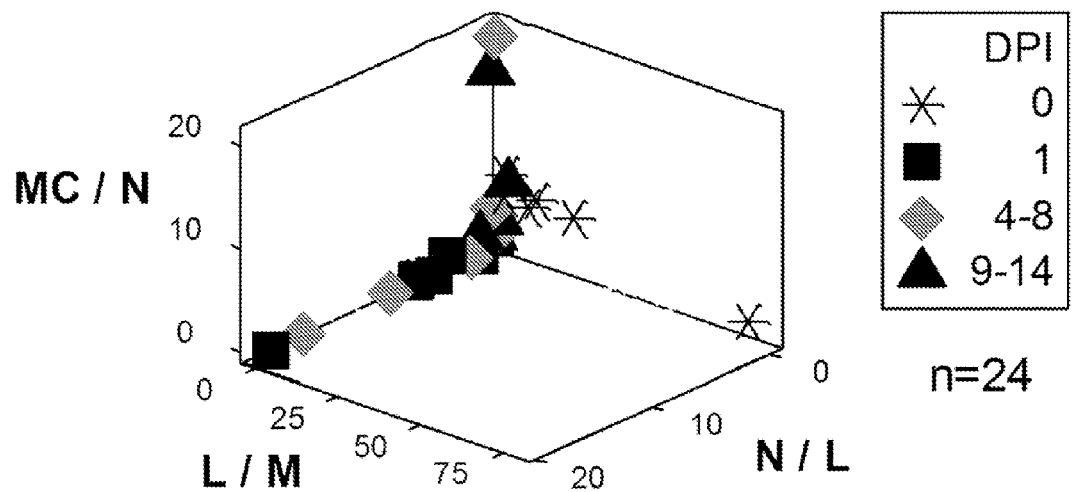
Figure 3E:
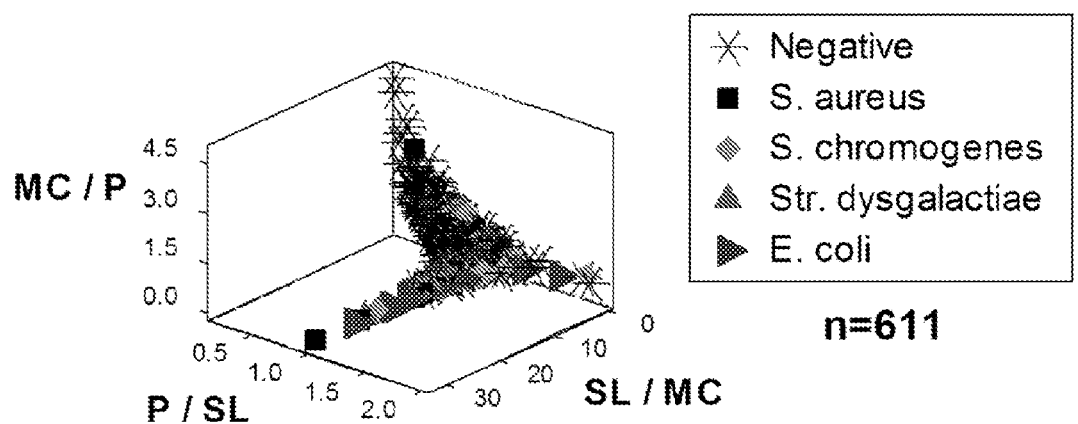
Figure 3F:
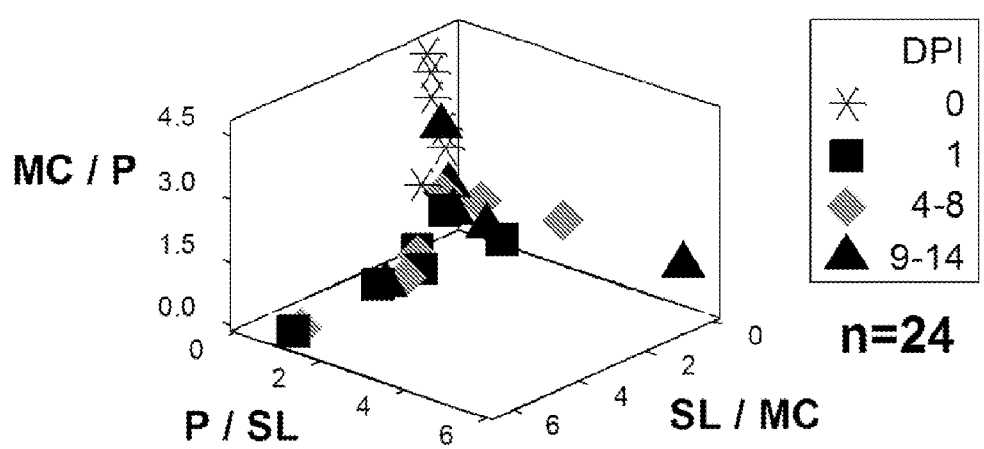
Figure 3G:
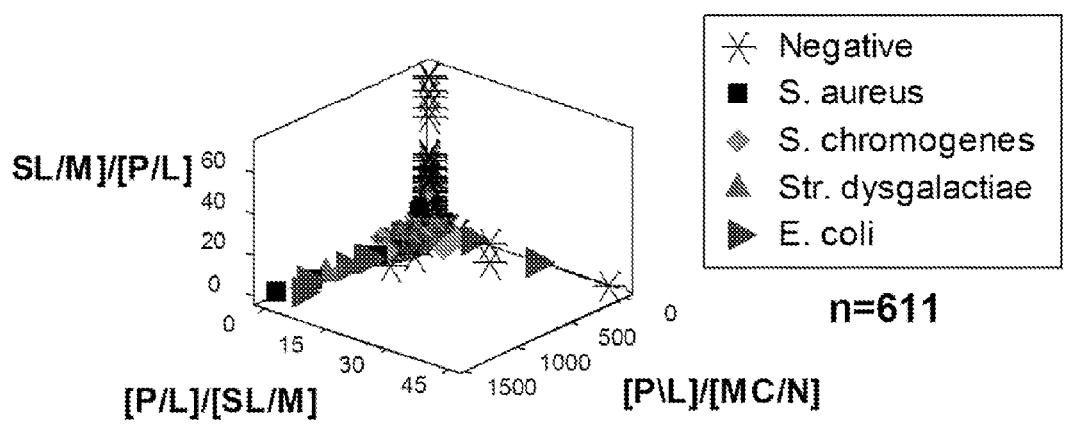
Figure 3H:
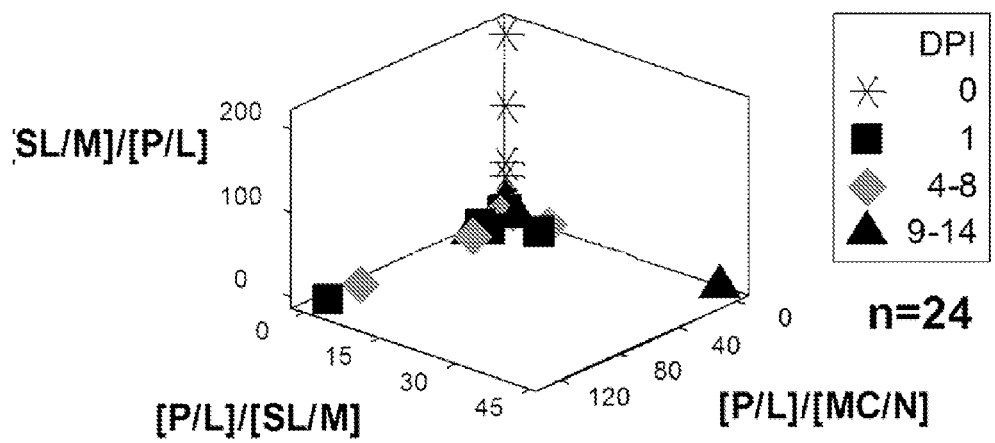

FIGS. 3A-H show bovine leukocyte data collected from two studies (one cross-sectional and non-experimental [n=611], and one longitudinal and experimental [n=6 cows, measured 4 times each, or 24 observations), according to one embodiment of the invention. In the longitudinal-experimental study, animals shown to be free of disease (day 0) were experimentally inoculated with Staphylococcus aureus and tested again at day[s] post-inoculation (DPI) 1, 4-8, and 9-14. In the cross-sectional, observational study, 4 bacterial species were isolated (S. aureus, S. chromogenes, Str. dysgalactiae, and E. coli). The use of one or more double ratios (such as the [P/L]/[MC/N]) reveals three perpendicular data inflections, which distinguish 'non-infected' ('0 DPI') observations from bacteria-positive ('infected' or later) observations (FIGS. 3A, B). Such pattern, potentially generated on real time, is here shown together with results obtained two days later (bacteriological test results). Such distinguishing pattern is not the result of a specific indicator: it can also be noticed when other indicators are investigated, provided that such indicators are similarly structured, i.e., at least one double ratio is measured (FIGS. 3C, D). However, not all indicators so structured provide the same information: while the structure shown in FIGS. 3A, B grouped all the bacteria-positive data points together, the structure used in C, D distinguished between early infections (1 DPI) and later infections (≥4 DPI, FIG. 3D). Other double-ratio based data structures also revealed perpendicular (non-overlapping) data patterns (FIGS. 3E-H). Therefore, the use of 3 leukocyte indicators structured to include, at least, one double ratio can both distinguish non-infected from infected individuals and, among infected individuals, can differentiate between those recently and non-recently infected. Such discrimination is independent of the infecting bacterial species (FIGS. 3A, C, E, G).

Figure 4A:
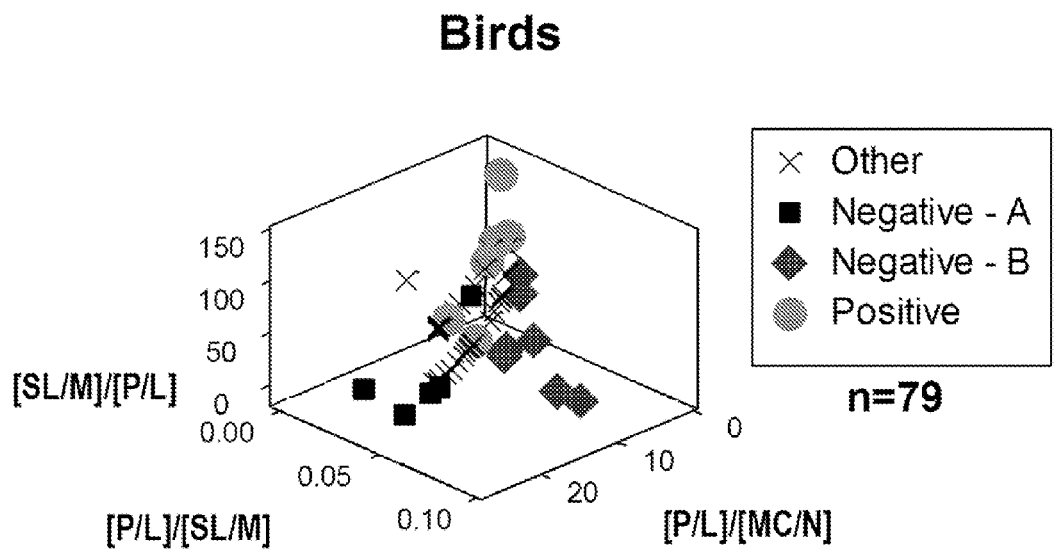
FIGS. 4A-D are graphs showing avian and mammalian data patterns according to one embodiment of the present invention.
Figure 4B:
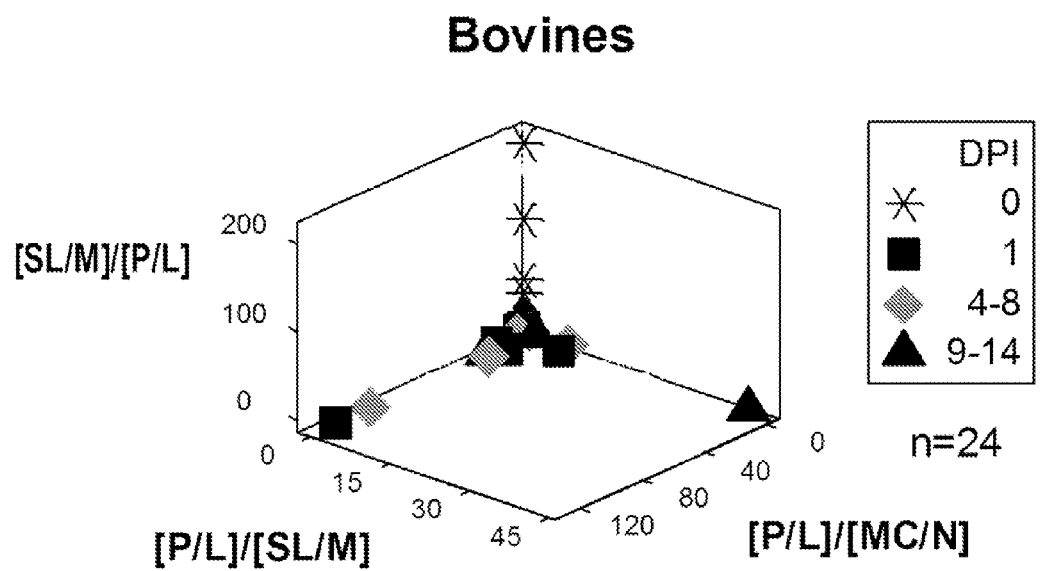
Figure 4C:
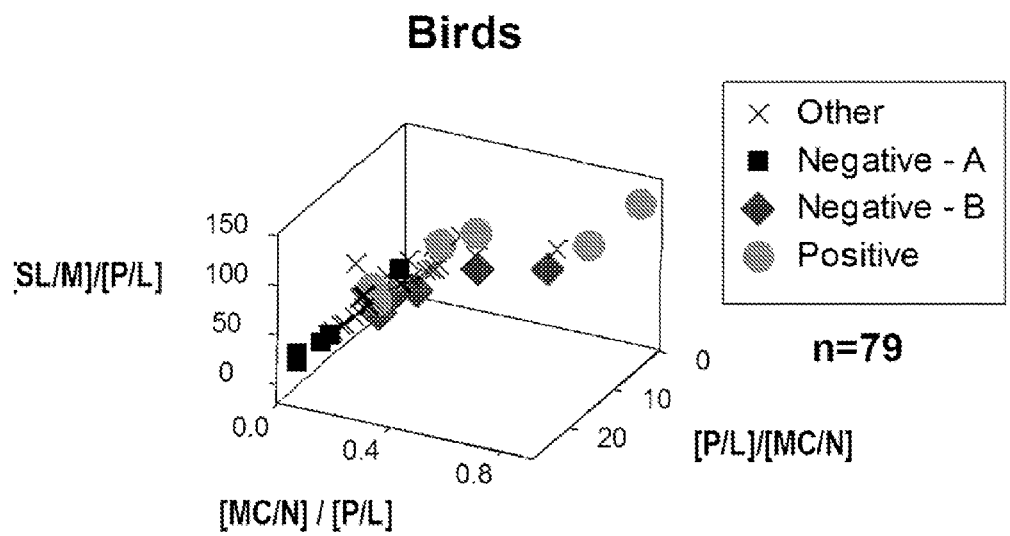
Figure 4D:
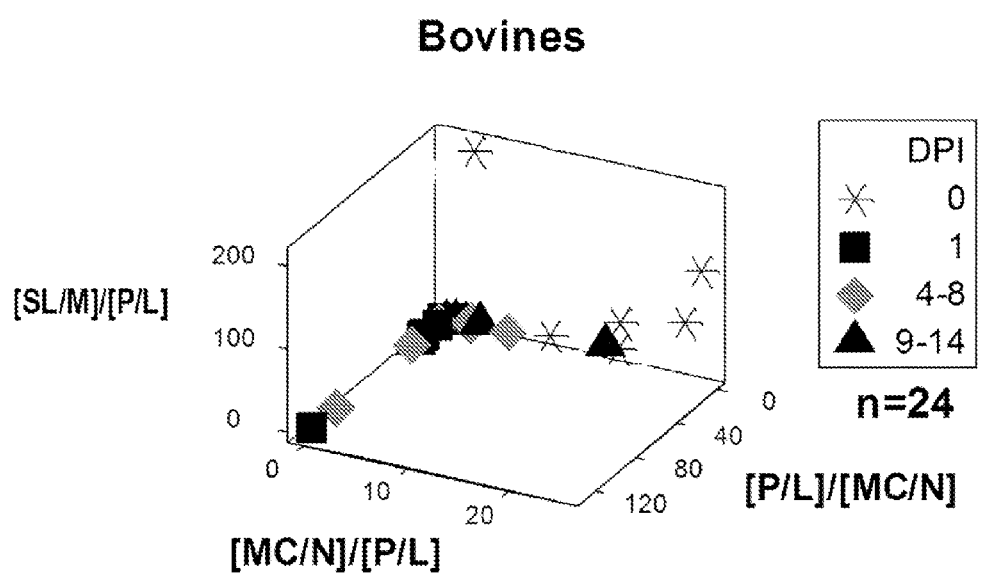

FIGS. 4A-D show avian and mammalian data patterns according to one embodiment of the invention. In spite of two major differences (mammalian vs. avian individuals, and bacterial vs. non-bacterial microorganisms), similar patterns were observed when the same indicators and the same data structure were applied (FIGS. 4A, B). The filaria-positive avian data subset (suspected to reflect a mutually beneficial bird-filaria relationship) coincided with the pattern shown by S. aureus-negative (non-infected) mammals (FIGS. 4A, B). Such discrimination and similar patterns were observed when other indicators, also structured as double ratios, were applied (FIGS. 4C, D). Therefore, the ability of leukocyte indicators to discriminate patterns associated with health is independent of the host species and also independent of the microbial species involved; i.e., some double leukocyte ratios possess 'universal' applications to distinguish health status.

Figure 5A:
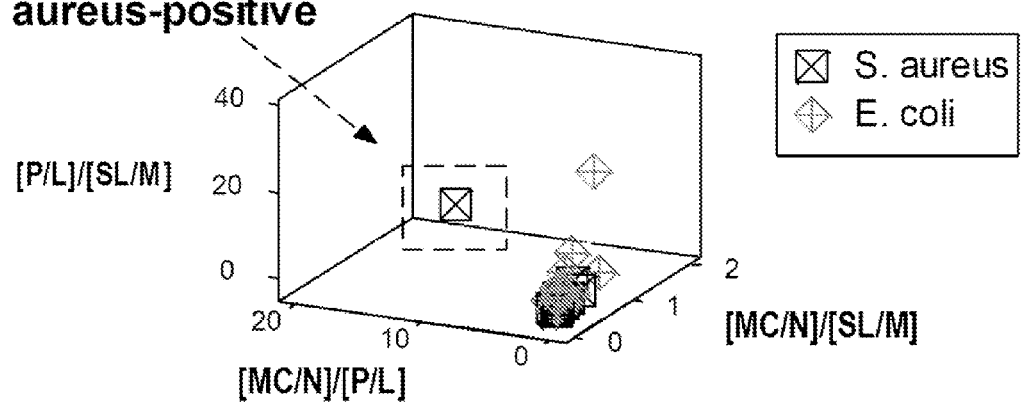
FIGS. 5A-F are graphs showing detection of false positives (true isolation of microbes, which do not necessarily reflect inflammation) according to one embodiment of the present invention.
Figure 5B:
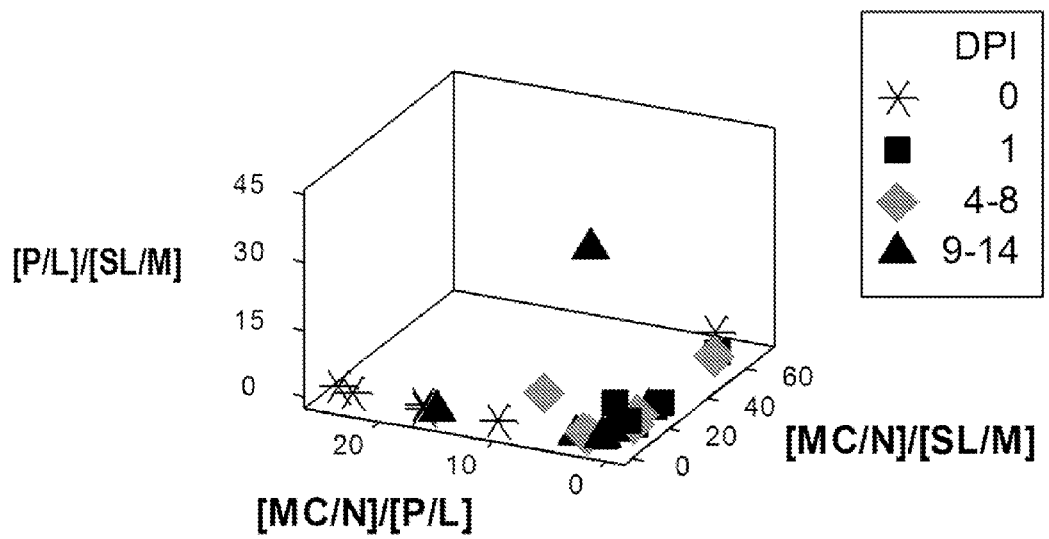
Figure 5C:
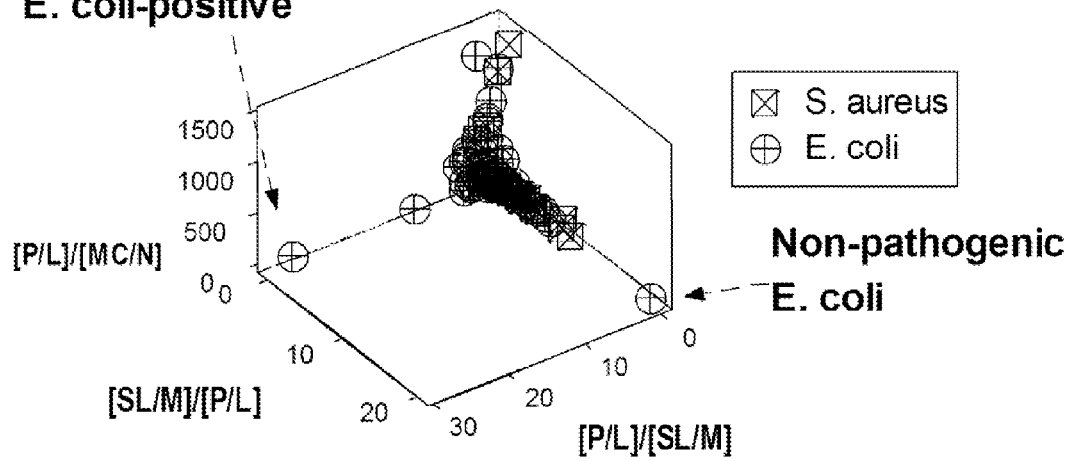
Figure 5D:
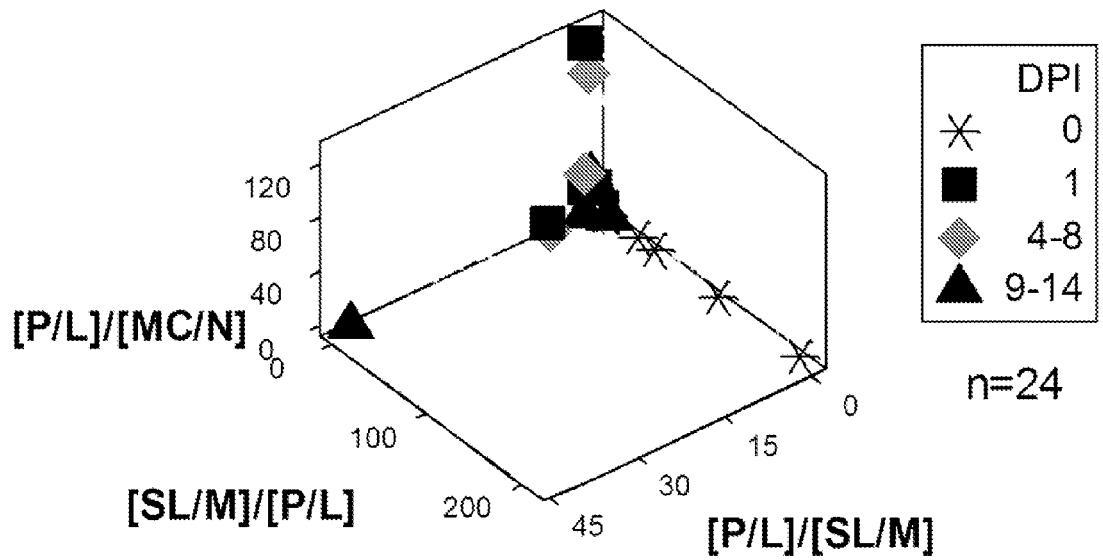
Figure 5E:
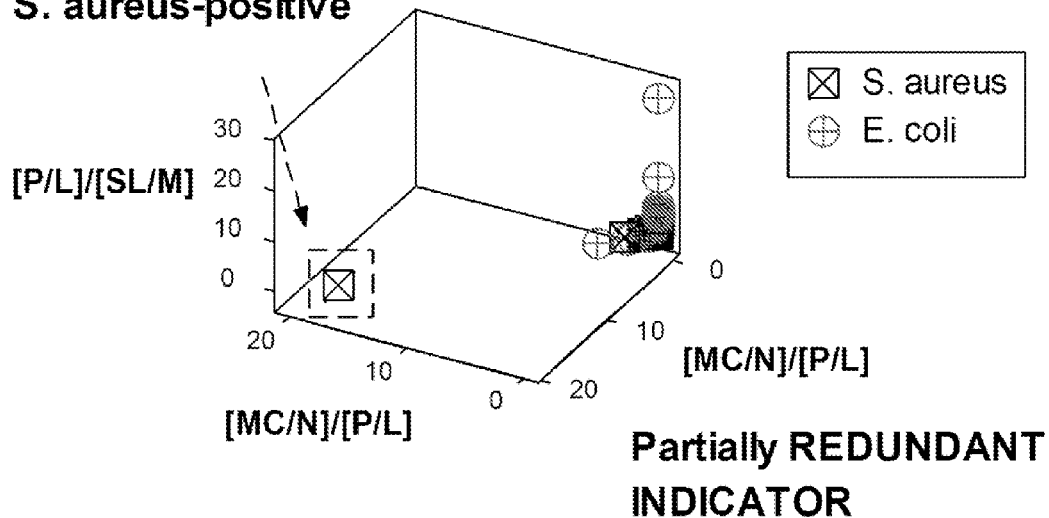
Figure 5F:
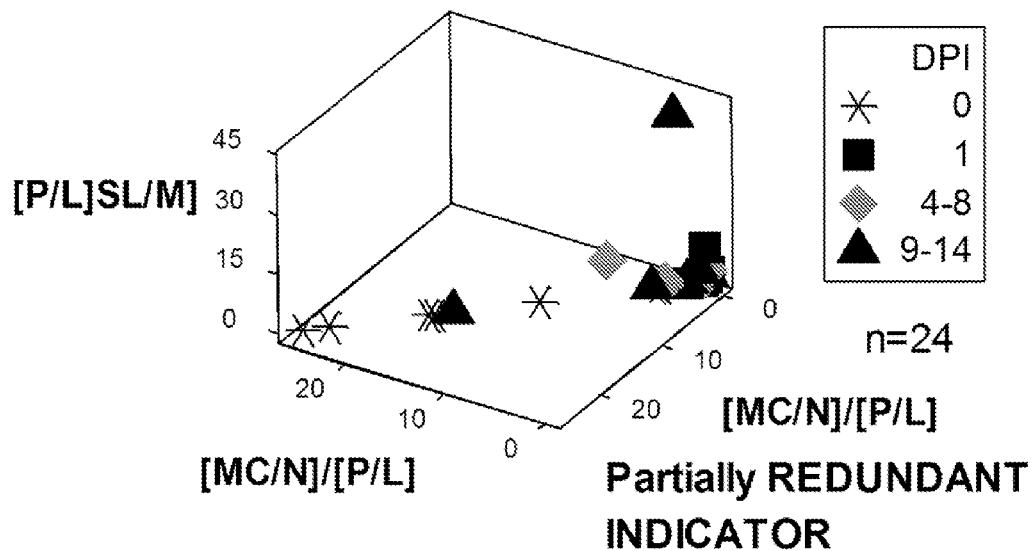

FIGS. 5A-F show detection of false positives (true isolation of microbes, which do not necessarily reflect disease or 'infection') according to one embodiment of the invention. Double leukocyte ratios can also distinguish observations that, if only bacteriological test results were considered, could be construed as 'positive' or 'infection', when, in fact, such positive isolations are not associated with an active disease process. That is shown in a subset of bovine observations, in which both S. aureus and E. coli were isolated (n=109). While 107 of all observations were clustered, one S. aureus observation differed from the rest on each of the 3 indicators assessed (FIG. 5A). Such pattern was consistent with either truly 'negative' (healthy and non-infected) individuals or a recovery process (FIG. 5B). Other double-ratio based indicators differentiated not only a late disease process (likely to be under recovery), but also an observation indicative of a non-pathogenic process (FIGS. 5C, D). When double-ratio based leukocyte indicators were constructed to be partially redundant (when the same indicator was assessed in two axes), some data subsets were compressed and other subsets were expanded. Such strategy allowed a better visualization of some observations, such as the fact that the S. aureus-positive observation mentioned above was clearly within the data range typical of non-infected individuals (FIGS. 5E, F). Hence, this method can detect individuals that, for instance, do not require treatment ('false positives').

Figure 6A:
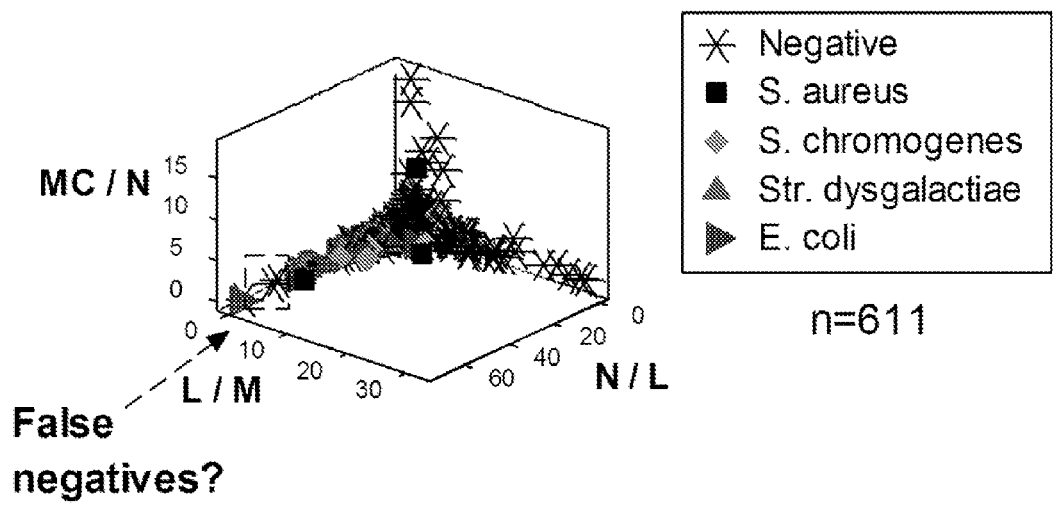
FIGS. 6A-D are graphs showing detection of false negatives and differentiation of two negative subsets according to one embodiment of the present invention.
Figure 6B:
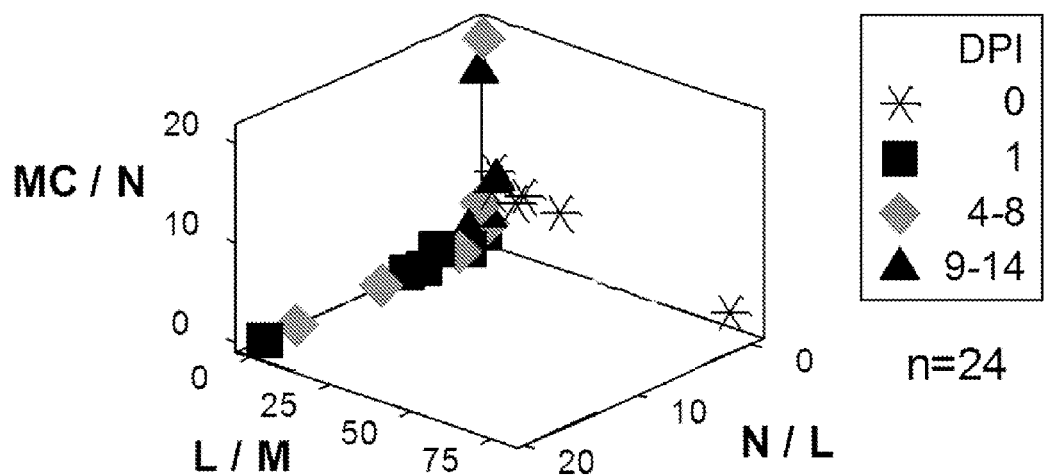
Figure 6C:
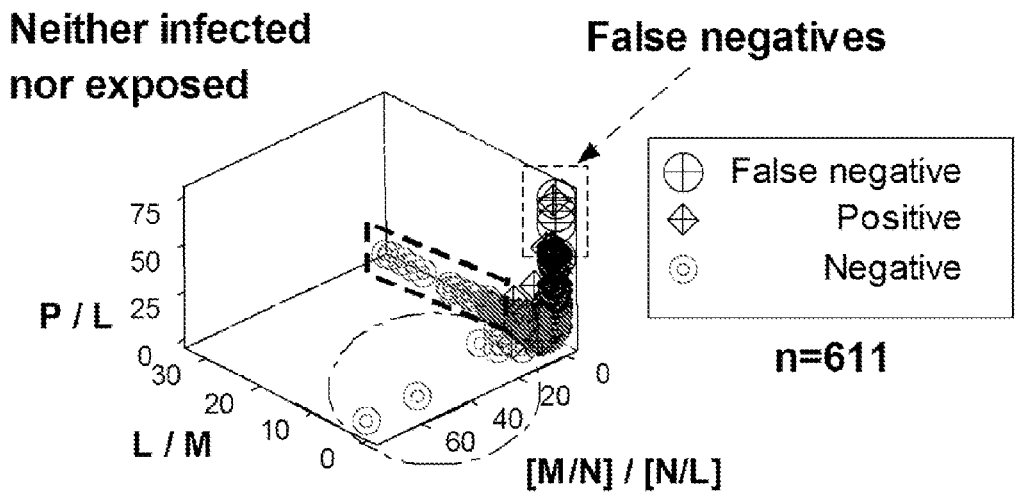
Figure 6D:
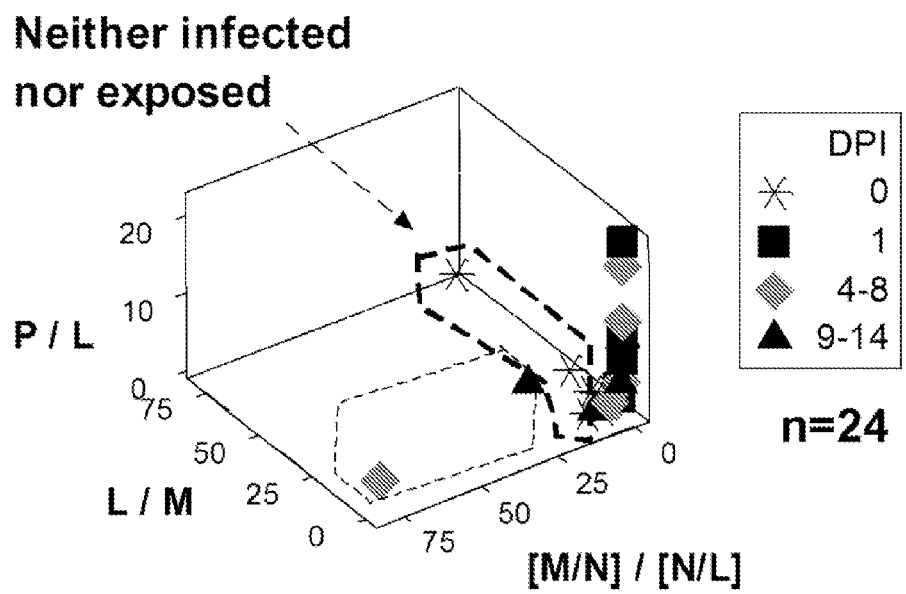
Figure 8A:
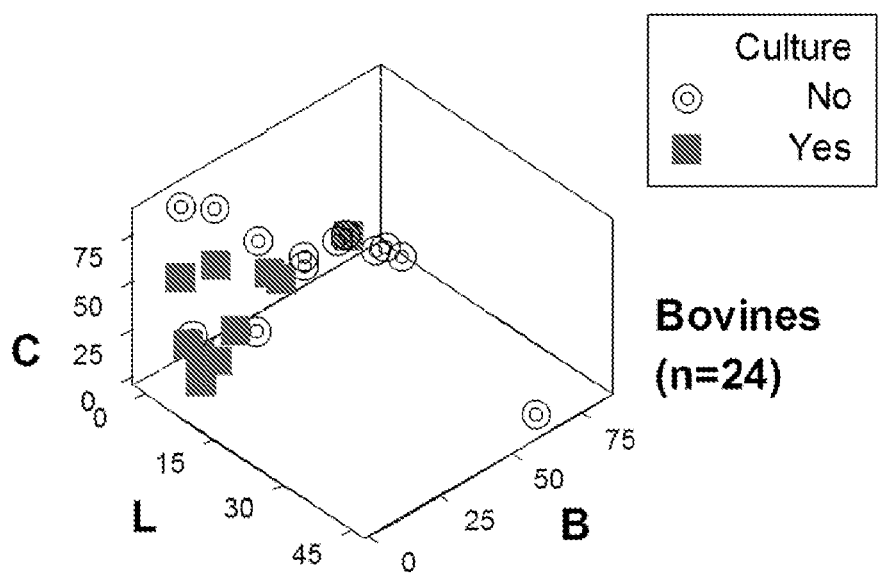
FIGS. 8A-F are graphs showing expanded 3-D combinations that are not informative according to one embodiment of the present invention.
Figure 8B:
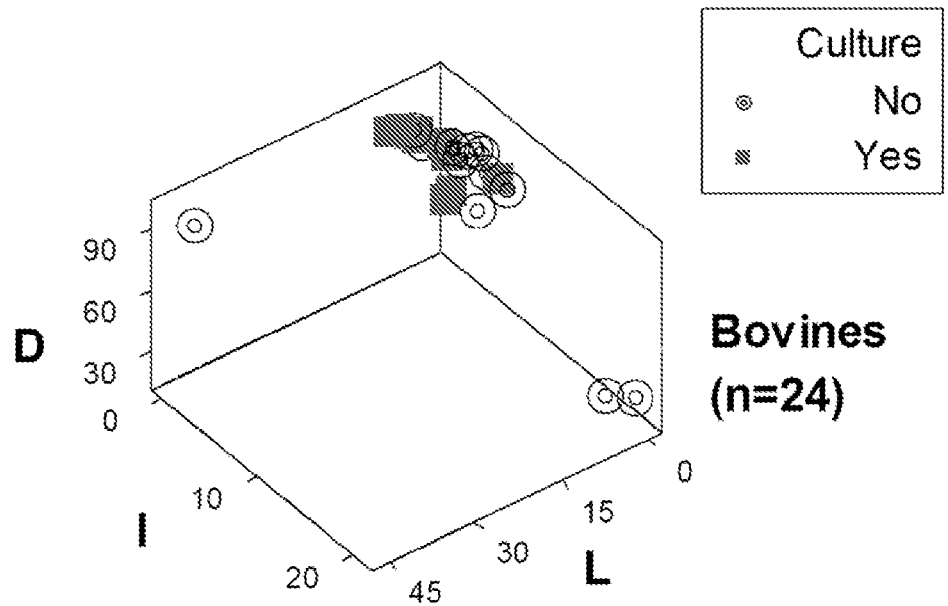
Figure 8C:
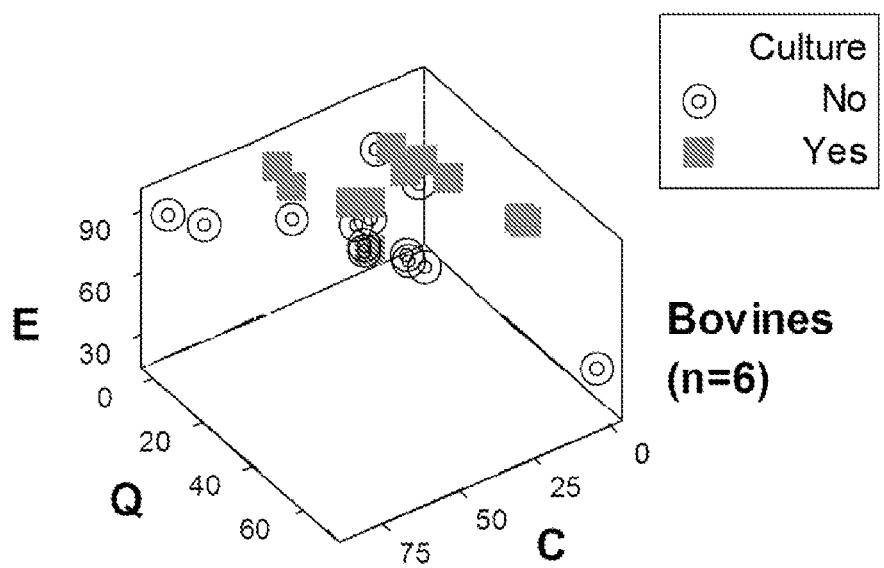
Figure 8D:
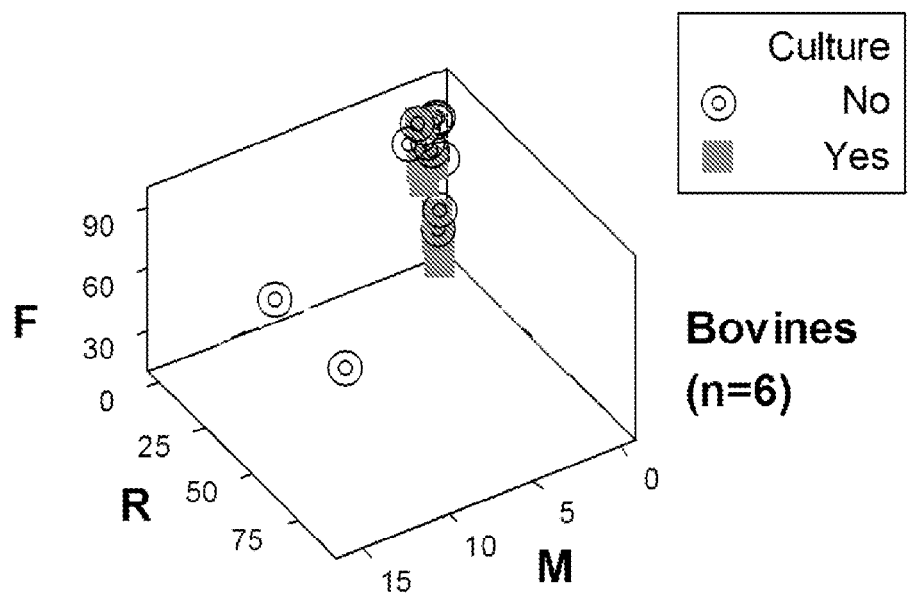
Figure 8E:
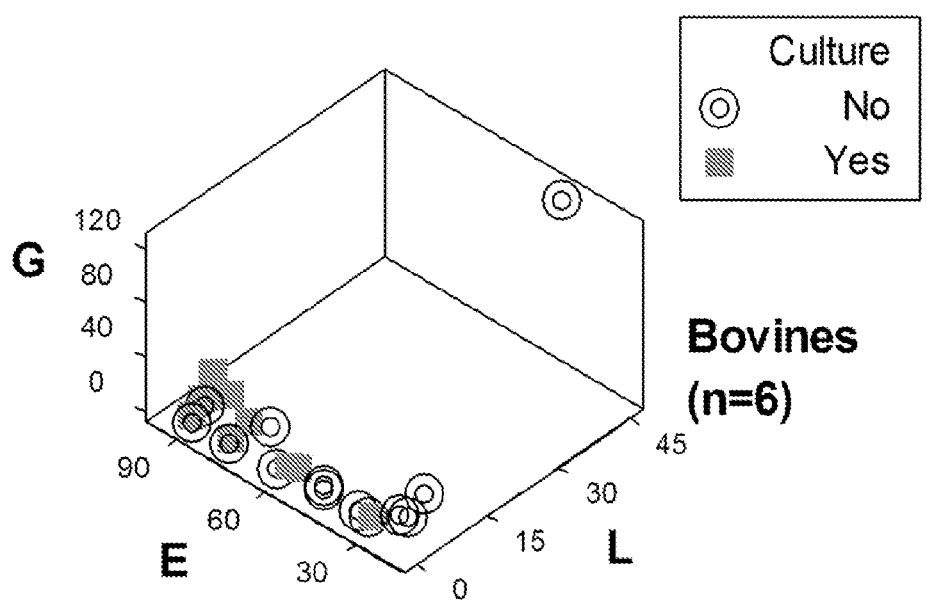
Figure 8F:
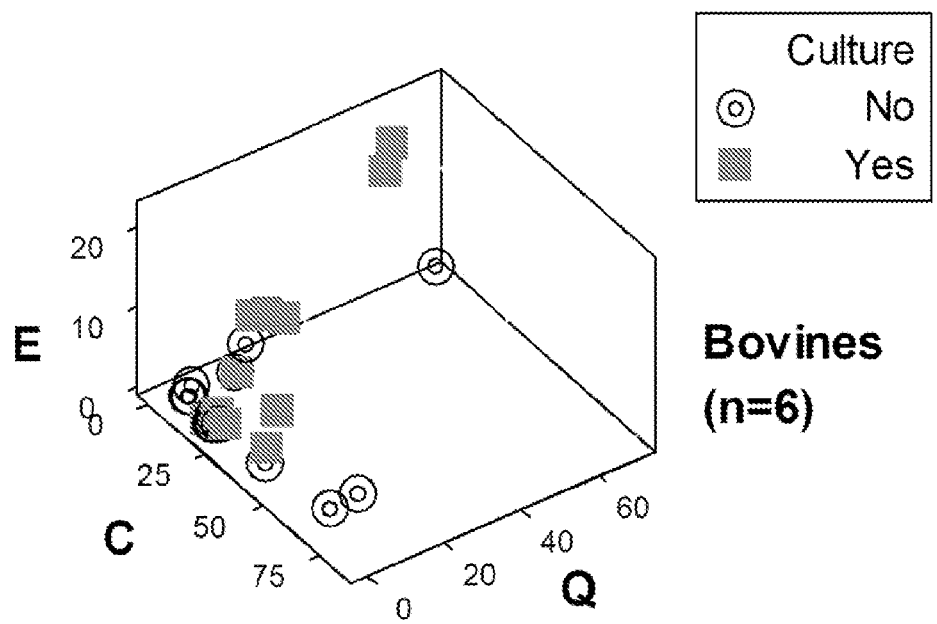

FIGS. 6A-D show detection of false negatives (no isolation of microbes, which may coexist with 'infection') and differentiation of two negative subsets ('neither exposed nor infected' and 'previously exposed or infected, now recovered') according to one embodiment of the present invention. When leukocytes indicators are structured as either single or double ratios (and at least one double ratio is considered), two or more 'negative' data subsets are distinguished by perpendicular data inflections. The subset located within a data region primarily composed of 'positive' ('infected') observations, can be regarded to be 'false negative' (arrow, FIG. 6A). Such location is perpendicular to the plane in which true 'non-infected' or 'negative' data points are observed (FIG. 6A). Other indicators—that share the same structure—also display such patterns (FIG. 6B). Given the perpendicular relationships of such 3 subsets, the data subset composed of individuals neither exposed nor infected to an infectious agent can be distinguished from the subset of individuals previously infected, although now recovered, and also differentiated from the 'false negative' subset (FIGS. 6C, D). Such discrimination is independent of bacterial species.

One exemplary embodiment of the present invention can be described as a method to detect and distinguish subsets of infected or non-infected individuals. The method comprises the steps of:

A) structuring primary leukocyte data of avian or mammalian species into compounded (secondary or post-secondary) data structures;

B) expanding the number of such secondary or post-secondary leukocyte data structures to create combinations that enhance (or compress) the expression of some health-related features of interest;

C) assessing such data structures within a space that simultaneously measures height, width, and depth (or three-dimensional [3D] space), so that data bifurcations, data inflections, and non-overlapping data distributions of various classes are visually detected and/or distinguished; and D) interpreting the meaning of such data structures, by considering data subsets that differ in their relative spatial location or are projected on different planes or dimensions, which distinguish subsets of different health classes, such as infected from non-infected individuals.

The method may detect and distinguish subsets of inflamed or non-inflamed individuals, by structuring primary leukocyte data (such as lymphocytes, macrophages, and neutrophils) into secondary and post-secondary data structures. This can be performed by:
  A) creating tables in which the counts and percentages of primary data (counts or relative percentages of lymphocytes, neutrophils, macrophages); and
  B) creating compounded (secondary) combinations, such as 'phagocytes' (the sum of macrophages and neutrophils), 'mononuclear cells' (the sum of lymphocytes and macrophages), and 'small leukocytes' (the sum of neutrophils and lymphocytes), which are expressed as counts or relative percentages.

The method expands the number of indicators by combining primary data into secondary and post-secondary data structures. This can be performed by:
  A) creating simple ratios, so that such ratios include two or more cell types, such as the percentage of neutrophils divided by the percentage of lymphocytes (or N/L ratio);
  B) creating complex ratios, so that elements of the numerator of one ratio are included in the denominator of the other ratio, such as the [MC/N]/[P/L] double ratio, in which lymphocytes (L) are both in the numerator of the first ratio (mononuclear cells or lymphocytes and macrophages [MC]) and in the denominator of the second ratio (the P/L ratio);
  C) creating partially redundant single ratios and measured with 3D plots, such as the set that includes: (i) the M/L ratio (plotted in axis X), (ii) the M/L ratio (plotted in axis Y), and (iii) some other indicator (plotted in axis Z);
  D) creating partially redundant double ratios and measured with 3D plots, such as the set that includes: (i) the [MC/N]/[P/L] ratio (plotted in axis X), (ii) the [MC/N]/[P/L] ratio (plotted in axis Y), and (iii) some other indicator (plotted in axis Z); and
  E) creating inverse (single or double) ratios and measured with 3D plots, such as the set that includes the L/N and the [L/P]/[N/MC] ratios, as well as some other indicator.

The method can generate distinct data patterns when the data structures are analyzed within a three-dimensional space. These data patterns comprise perpendicular data inflections, data bifurcations, perpendicular relationships between data subsets of different classes, and non-overlapping data distributions of different data classes, whether within the same axis or across axes perpendicular to one another.

The method may generate information applicable to decision-making by:
  A) interpreting as 'non-infected' (or similar denominations) the data subset reported along an axis perpendicular to (one or two) dimensions predominantly occupied by 'infected' (or similar denominations) data points, and vice versa;
  B) interpreting as 'false positives' (or similar denominations) data points that indicate 'infection' according to some test, when such data points are spatially far or perpendicular from the location of most 'positive' data points;
  C) interpreting as 'false negatives' (or similar denominations) data points that indicate 'no infection' according to some test, when such data points are located at a far spatial distance or perpendicular from the location of most 'negative' data points, and/or such data points are within a data region predominantly composed of 'positive' observations;
  D) interpreting as 'neither exposed nor infected' (or similar denominations) data points that (a) do not share patterns with 'infected' observations, and (b) are located perpendicular to or far from other 'negative' data points, if the second subset shares patterns with 'infected' observations; and
  E) interpreting as 'previously exposed or infected, now recovered' (or similar denominations) data points that are located far from or perpendicular to both other 'negative' data points and early 'infected' observations.

The invention can detect and distinguish subsets of mammalian and avian animals through real time differentiation of non-overlapping data subsets, whether considering or not considering other (bacteriological or parasite-related) tests, consideration of similar patterns shared across (avian and/or mammalian) species, and consideration of similar patterns observed across bacterial species.

This method reveals the three major characteristics complex biological systems display: (i) 'emergence' or 'novelty', i.e., new information emerges when the data are structured to possess higher complexity, i.e., when a 'high-' or system-level' data structure is assembled (a characteristic not shown when 'low-level', 'elementary' or 'primary') structures, such as the data collected from the field or observed in nature) are analyzed; (ii) 'irreducibility' (the functions or patterns revealed at the system level are not found at or explained by 'low-level' variables, such as a given cell type); and (iii) 'unpredictability' (analysis of 'low-level' variables cannot predict 'emergence').

FIGS. 2A-F illustrate while classic approaches—those that measure 'low-level'/non-complex variables, such as the percent of each cell type—do not discriminate (FIGS. 2A, B), distinct and informative patterns are detected when the present invention is applied (FIGS. 2C-F). While the classic approach does not distinguish two discrete categories (FIGS. 2A, B), the same data, when assessed by this invention provides new information (three subsets were differentiated), in real time (FIGS. 2C-H).

The invention can extract new or additional information in real time. In one example, due to the combinatorial properties of the method, as well as redundancy, it is possible to expand (or compress) the expression of a specific pattern, so a data point or subset of particular interest can be investigated (an additional strategy that results in new or more information, FIGS. 5E, F).

FIGS. 5E, F illustrate the invention's ability to perform pattern clarification. In other words, the invention can add emphasis based on partial redundancy. Partial redundancy (assessing the same variable, twice) magnifies the expression of some findings. In this example, a bacterium-positive data point (lower left, FIG. 5E) is analyzed within a structure designed to expand the expression of truly negative observations. Such data structure locates the observation of interest far from the remaining bacterium-positive observations (FIG. 5E) but within the data range of bacterium-negative observations (experimental and longitudinal data, used for comparison, FIG. 5F). Thus, the observation shown in FIG. 5E is suspected to be a false-positive. Such effect is not the result of the variables investigated, but the result of using the same variable, twice, which occupies the diagonal of the rectangle.

An additional strategy is to assess the same variable, at least twice, in opposite positions (as the numerator of one variable and the denominator of the other variable(s)). For instance, the P/L vs. the L/M, as well as the P/L vs. the [M/N]/[N/L] data structures possess such design (FIG. 6C). FIGS. 6C, D illustrate enhanced discrimination due to opposite positioning of the same variable. Both false negatives and two sets of 'negatives' ('neither currently nor previously inflamed' and 'previously inflamed but not inflamed anymore or recovered') can be inferred by observational (FIG. 6C) and experimental (FIG. 6D) data.

The present invention does not rely on the primary input or secondary (combinatorial) data assessed. The present invention does not depend on any number of any variable. Instead, the invention selects and interprets plots that reveal, at least, functional data integrity, reduced data variability, 3D interactions, and complexity. The invention—identifies distinct or non-random patterns, such as perpendicular data inflections. Based on objective (visual and numerical) information, the various principles discussed above are demonstrated after (not before) the method is conducted. The values of interactions of interest are retrieved, even when there is no prior knowledge on the biological meaning of such interactions and/or such interactions are not explicitly investigated by the method.

Such design results in a counter-intuitive feature: no number or variable is critical. Yet, useful information, not explicitly considered, may be obtained (a consequence of unpredictability, one of the three basic properties of complex systems). Provided that, at least, functional data integrity, reduced data variability, complexity, and distinct patterns are shown in 3D space, any data structure derived from the input data can extract more or new information from the same data.

Another embodiment of the method is described below. The first step of this embodiment is data structuring (FIG. 7). The first step is composed of two phases: (i) data input, and (ii) creation of secondary/post-secondary data structures. In this step, any set of leukocyte data combinations (an expanded table, with more columns than the input table), of any size can be used, provided that (a) at least one of the new columns created includes one complex ratio, and (b) at least a pair of columns (whether input, secondary, or combinations of), when measured in 3D space, meets these conditions: (i) measures all data points of all input variables; (ii) includes at least, one simple ratio, i.e., the percentage of one variable over the percentage of another variable, whether input or secondary, and (iii) displays a single, one data-point wide line of observations.

One example of this method can be illustrated through publicly available data for bovines inoculated with a pathogen-*S. aureus*. (Rivas A L, et al. Longitudinal evaluation of bovine mammary gland health status by somatic cell counts, flow cytometry and cytology. *J Vet Diagn Invest* 13: 399-407; 2001). Three columns of continuous data (percent), and one column of discontinuous data (days post-inoculation) are presented as table I.

TABLE I

| Cow ID # | DPI (day[s] post-inoculation) | Lymphocyte (L) % | Polymorpho-nuclear cell (PMN or N) % | Macrophage/monocyte (M) % |
|---|---|---|---|---|
| A | 0 | 79.5 | 14.2 | 6.3 |
| B | 0 | 81.6 | 15.0 | 3.4 |
| C | 0 | 68.8 | 11.5 | 19.7 |
| D | 0 | 63.0 | 36.2 | 0.8 |
| E | 0 | 76.7 | 16.0 | 7.3 |

TABLE I-continued

| Cow ID # | DPI (day[s] post-inoculation) | Lymphocyte (L) % | Polymorpho-nuclear cell (PMN or N) % | Macrophage/monocyte (M) % |
|---|---|---|---|---|
| F | 0 | 65.1 | 15.2 | 19.7 |
| A | 1 | 9.8 | 68.8 | 21.4 |
| B | 1 | 28.8 | 60.0 | 11.2 |
| C | 1 | 43.6 | 37.1 | 19.3 |
| D | 1 | 13.4 | 75.4 | 11.2 |
| E | 1 | 4.4 | 85.6 | 10.0 |
| F | 1 | 9.7 | 41.9 | 48.4 |
| A | 4-8 | 23.3 | 4.6 | 72.0 |
| B | 4-8 | 52.2 | 29.4 | 18.4 |
| C | 4-8 | 8.0 | 73.0 | 19.0 |
| D | 4-8 | 23.2 | 62.9 | 13.9 |
| E | 4-8 | 5.1 | 85.0 | 9.9 |
| F | 4-8 | 38.1 | 18.7 | 43.2 |
| A | 9-14 | 10.8 | 5.4 | 83.8 |
| B | 9-14 | 53.2 | 24.4 | 22.4 |
| C | 9-14 | 40.6 | 34.9 | 24.4 |
| D | 9-14 | 22.6 | 34.2 | 43.2 |
| E | 9-14 | 9.7 | 75.5 | 14.8 |
| F | 9-14 | 69.8 | 12.8 | 17.4 |

Utilizing input data, the method creates data combinations (secondary/post-secondary data, as described below). Due to both brevity and to demonstrate that the content of each secondary data structure is irrelevant (provided that each column is a combination derived from Table I and meets the conditions described before) the columns of Table II do not show leukocyte descriptors. Instead, letters are used as descriptors.

Combinations of primary data are created by a computer algorithm. The purpose of such algorithm is to create a large number of combinations derived from the input data, as described in the following example. Based on data from three cell types (e.g., the percent of 3 cell types named A, B, C), combinations can include: A+B, A+C, B+C, [A+B]/C, [A+C]/B, [B+C]/A, A/B, A/C, B/C, [A/B]/[B/C], [A/C]/[C/B], [A/B]/[C/B], [B/A]/[B/C], . . . . If four cell types are considered (A-D) additional combinations are created, i.e., A+B+C, A+B+D, A+C+D, [A+B+C]/D, [A+B+D]/C, . . . .

Each column of Table II includes (combinatorial) data derived from two or more of the original 3 (or more) columns. The following example includes only some of the compounded indicators this method can generate (this method can create a virtually infinite number of combinations). The first 3 columns (A-C, those of Table I) are also considered when 3-D plots are generated. Values shown in Table II are combinations (functions) derived from columns A-C, not measures of actual entities, i.e., Table II values cannot be found in nature. Any combination created from the input data can be applied, provided that when pairs are considered, (i) all data points of all input data are considered, (ii) at least one ratio is included, and (iii) a single line of one-data point wide observations can be noticed in, at least, one perspective of the 3-D plot so created.

TABLE II

| Cow # | DPI | D | E | F | G | H | I | J | K | L | M | N | O | P | Q | R | S | T |
|---|---|---|---|---|---|---|---|---|---|---|---|---|---|---|---|---|---|---|
| A | 0 | 93.7 | 20.5 | 85.8 | 14.8 | 0.2 | 6.0 | 0.17 | 5.5 | 2.2 | 0.4 | 12.6 | 0.07 | 57.6 | 2.4 | 0.40 | 23.4 | 0.04 |
| B | 0 | 96.6 | 18.4 | 85.0 | 28.41 | 0.22 | 5.66 | 0.18 | 5.44 | 4.41 | 0.22 | 24.0 | 0.04 | 126.00 | 5.01 | 0.19 | 25.1 | 0.04 |
| C | 0 | 80.3 | 31.2 | 88.5 | 4.076 | 0.45 | 7.69 | 0.16 | 5.98 | 0.58 | 1.71 | 3.49 | 0.28 | 8.98 | 0.52 | 1.88 | 16.9 | 0.05 |
| D | 0 | 99.2 | 37.0 | 63.8 | 124.0 | 0.58 | 1.76 | 0.57 | 1.74 | 45.2 | 0.02 | 78.7 | 0.01 | 211.1 | 70.3 | 0.01 | 3.00 | 0.33 |
| E | 0 | 92.7 | 23.3 | 84.0 | 12.69 | 0.30 | 5.25 | 0.20 | 4.79 | 2.19 | 0.45 | 10.5 | 0.09 | 41.8 | 2.41 | 0.41 | 17.2 | 0.05 |
| F | 0 | 80.3 | 34.9 | 84.8 | 4.076 | 0.53 | 5.57 | 0.23 | 4.28 | 0.77 | 1.29 | 3.30 | 0.30 | 7.60 | 0.73 | 1.36 | 10.4 | 0.09 |
| A | 1 | 78.6 | 90.2 | 31.2 | 3.673 | 9.20 | 0.45 | 7.02 | 0.14 | 3.21 | 0.31 | 0.45 | 2.18 | 0.39 | 8.09 | 0.12 | 0.04 | 20.2 |
| B | 1 | 88.8 | 71.2 | 40.0 | 7.929 | 2.47 | 0.66 | 2.08 | 0.48 | 5.35 | 0.18 | 2.57 | 0.38 | 3.20 | 11.8 | 0.08 | 0.26 | 3.70 |
| C | 1 | 80.7 | 56.4 | 62.9 | 4.181 | 1.29 | 1.69 | 0.85 | 1.17 | 1.92 | 0.52 | 2.25 | 0.44 | 3.23 | 2.46 | 0.40 | 1.31 | 0.76 |
| D | 1 | 88.8 | 86.6 | 24.6 | 7.929 | 6.46 | 0.32 | 5.62 | 0.17 | 6.73 | 0.14 | 1.19 | 0.83 | 1.22 | 24.3 | 0.04 | 0.05 | 19.8 |
| E | 1 | 90.0 | 95.6 | 14.4 | 9.000 | 21.2 | 0.16 | 19.4 | 0.05 | 8.56 | 0.11 | 0.44 | 2.27 | 0.41 | 53.5 | 0.01 | 0.00 | 129. |
| F | 1 | 51.6 | 90.3 | 58.1 | 1.066 | 9.30 | 1.38 | 4.31 | 0.23 | 0.86 | 1.15 | 0.20 | 4.98 | 0.11 | 0.76 | 1.30 | 0.14 | 6.71 |
| A | 4 | 27.9 | 76.6 | 95.3 | 0.387 | 3.28 | 20.7 | 0.19 | 5.06 | 0.06 | 15.6 | 0.32 | 3.09 | 0.11 | 0.01 | 53.4 | 6.30 | 0.15 |
| B | 4 | 81.6 | 47.8 | 70.6 | 4.435 | 0.91 | 2.40 | 0.56 | 1.77 | 1.59 | 0.62 | 2.83 | 0.35 | 4.84 | 1.84 | 0.54 | 2.62 | 0.38 |
| C | 4 | 81.0 | 92.0 | 27.0 | 4.263 | 11.5 | 0.36 | 9.12 | 0.10 | 3.84 | 0.26 | 0.42 | 2.37 | 0.37 | 11.5 | 0.08 | 0.03 | 31.0 |
| D | 4 | 86.1 | 76.8 | 37.1 | 6.194 | 3.31 | 0.58 | 2.71 | 0.36 | 4.52 | 0.22 | 1.66 | 0.59 | 1.87 | 10.5 | 0.09 | 0.17 | 5.61 |
| E | 4 | 90.1 | 94.9 | 15.0 | 9.101 | 18.6 | 0.17 | 16.6 | 0.06 | 8.58 | 0.11 | 0.51 | 1.94 | 0.48 | 51.5 | 0.01 | 0.00 | 105. |
| F | 4 | 56.8 | 61.9 | 81.3 | 1.315 | 1.62 | 4.34 | 0.49 | 2.03 | 0.43 | 2.31 | 0.88 | 1.13 | 0.80 | 0.30 | 3.30 | 2.67 | 0.37 |
| A | 9 | 16.2 | 89.2 | 94.6 | 0.193 | 8.25 | 17.5 | 0.50 | 2.00 | 0.06 | 15.5 | 0.12 | 7.75 | 0.02 | 0.01 | 90.6 | 2.12 | 0.47 |
| B | 9 | 77.6 | 46.8 | 75.6 | 3.464 | 0.87 | 3.09 | 0.45 | 2.18 | 1.08 | 0.91 | 2.37 | 0.42 | 3.93 | 1.1 | 0.89 | 3.52 | 0.28 |
| C | 9 | 75.5 | 59.3 | 65.0 | 3.094 | 1.46 | 1.86 | 0.85 | 1.16 | 1.43 | 0.69 | 1.66 | 0.60 | 2.11 | 1.6 | 0.60 | 1.27 | 0.78 |
| D | 9 | 56.8 | 77.4 | 65.8 | 1.315 | 3.42 | 1.92 | 1.51 | 0.66 | 0.79 | 1.26 | 0.52 | 1.91 | 0.38 | 0.6 | 1.46 | 0.56 | 1.78 |
| E | 9 | 85.2 | 90.3 | 24.5 | 5.757 | 9.30 | 0.32 | 7.78 | 0.12 | 5.10 | 0.19 | 0.65 | 1.52 | 0.61 | 17.7 | 0.05 | 0.03 | 28.6 |
| F | 9 | 82.6 | 30.2 | 87.2 | 4.747 | 0.43 | 6.81 | 0.18 | 5.45 | 0.73 | 1.35 | 4.01 | 0.24 | 10.9 | 0.6 | 1.43 | 15.7 | 0.06 |

The next step of this embodiment is data expansion. In this step, 3-D expressions of data combinations reveal a single, one data point-wide, line of observations. Such a line is observed under some angle or perspective, i.e., to detect a single line, plots may require to be rotated. Similar plots may differ in the angle under which they are assessed. However, not all expanded, 3-D combinations are informative (FIGS. 8A-F).

Figure 9A:
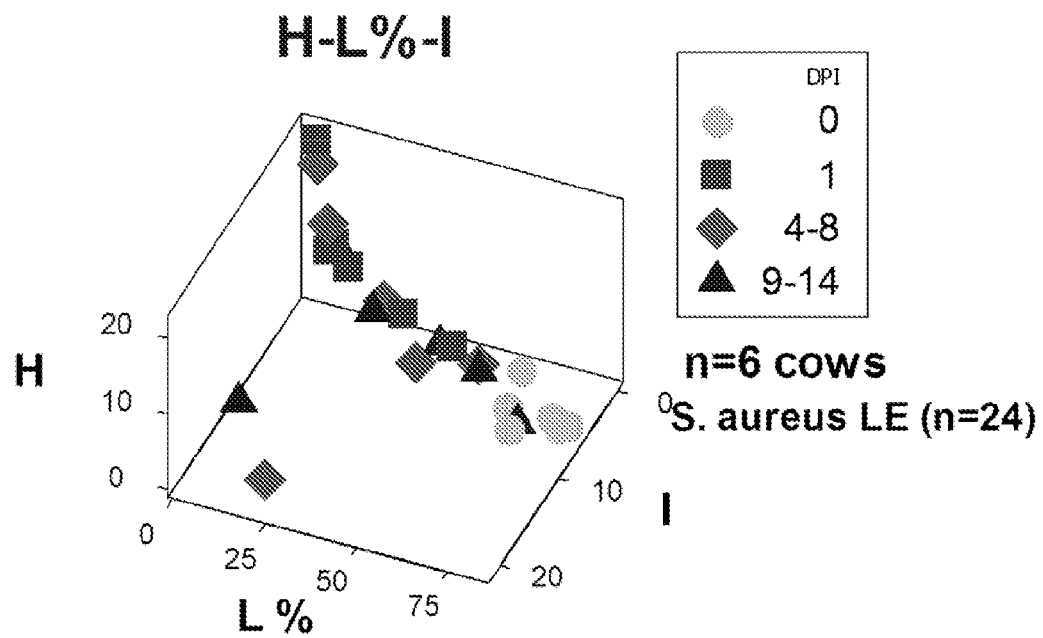
FIGS. 9A-B are graphs showing patterns which facilitate discrimination according to one embodiment of the present invention.

Using the data shown in Table II, the method creates numerous 3-D data structures of which only those that reveal distinct patterns are selected, according to the objective decision rules described in the next step (FIGS. 9A, B).

The next step of this embodiment is data assessment. In this step, there are two sub-steps: pattern recognition and data recovery. Pattern recognition involves the objective selection of informative patterns such as perpendicular data inflections. Data recovery involves recovering both the data values of the variables investigated and those of any informative variable or variables, regardless of whether the variable(s) was/were explicitly investigated when 3D plots were created.

Distinct 3D patterns reveal non-random patterns, such as perpendicular data inflections (patterns that involve two or more planes), data bifurcations, and/or data clusters. Such patterns facilitate discrimination: subsets can be distinguished, as shown in FIGS. 9A, B. Two 3D plots, generated from the data shown in Tables I and II are shown. While they share some patterns, they also differ in one aspect. Both FIGS. 9A and 9B differentiate all 0 day post-inoculation (0 DPI) from all 1-DPI data points, i.e., either plot could be considered to distinguish non-infected individuals from recently infected (1 DPI) individuals. FIG. 9A demonstrates that each end of a rather single line of observations show biologically distinct (non-infected vs. infected) conditions. However, FIG. 9A does not show a clear cut or threshold, i.e., it is difficult (and may lead to errors) to use FIG. 9A with the purpose of differentiating non-infected from infected individuals.

Figure 9B:
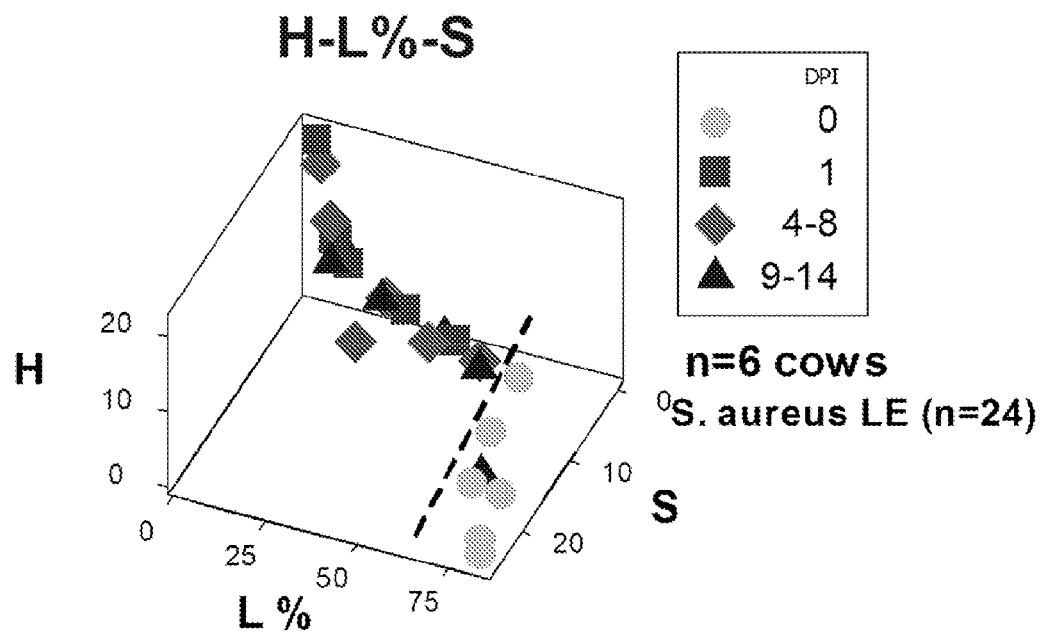

In contrast, FIG. 9B—which only differs in one of the 3 axes—reveals a quasi-perpendicular data inflection (an inflection that involves a different plane, broken line, FIG. 9B). Such inflection is the result of interactions not yet known (although observed). Because it displays a perpendicular data inflection that involves all planes (broken line, FIG. 9B), FIG. 9B can distinguish, without any pre-selected cut-off point or assumption, all non-infected from all infected individuals (except one 9-14 DPI data point).

When distinct patterns are observed, plots are selected according to a decision rule: (i) Rank #1 (first priority): triple perpendicular data inflections, together with clusters and/or data bifurcations; (ii) Rank #2 (second priority): three perpendicular data inflections; (iii) Rank #3 (third priority): one or two perpendicular data inflection(s); (iv) Rank #4 (fourth priority) Data clusters or bifurcations.

Because FIG. 9B displays the first priority, the method selects such plot.

Using the primary data shown in Table I and considering the patterns shown by FIGS. 9A, B the raw data of the subset distinguished by a perpendicular data inflection (DPI 0 observations can be retrieved. For instance, 0-DPI data points are characterized by:
(i) higher L %,
(ii) higher M %,
(iii) higher MC %,
(iv) lower N %,
(v) lower P/L,
(vi) greater MC/N,
(vii) greater SL/M,
(viii) greater [MC/N]/[P/L], and
(ix) greater [SL/M]/[P/L] ratios than the remaining observations (numerous other inferences can also be deduced).

Such inferences are based on the following:

All 0-DPI data points had a lower P/L value than later observations. Such conclusion is based on the fact that values of PMN+M % (phagocytes or P) ranged, at day 0, between 18.4 (cow B, Table IA) and 37% (cow D, Table IA). Consequently, the remaining cell type (the lymphocyte or L) exceeded 63% at 0-DPI. Therefore, the P/L ratios of all 0-DPI observations are lower than 1. By achieving such conclusion it is demonstrated that all values of all cell types were assessed (one of the properties or requirements of the method was achieved), i.e., the 0 DPI subset was not assessed in terms of the input data (separate cell types, Table I) but as a system.

While such inferences, to be made, do not require the generation of any 3D plot, the creation of a 3D plot that reveals a distinct (quasi-perpendicular) data inflection generates two non-overlapping data subsets.

In addition, it is demonstrated that no numerical 'cut-off' value is required to distinguish non-overlapping subsets: perpendicular data inflections (visually observable features) differentiate subsets, regardless of any numerical value. Hence, the present invention is a solution for the 'cost of dichotomization' problem.

Figure 10A:
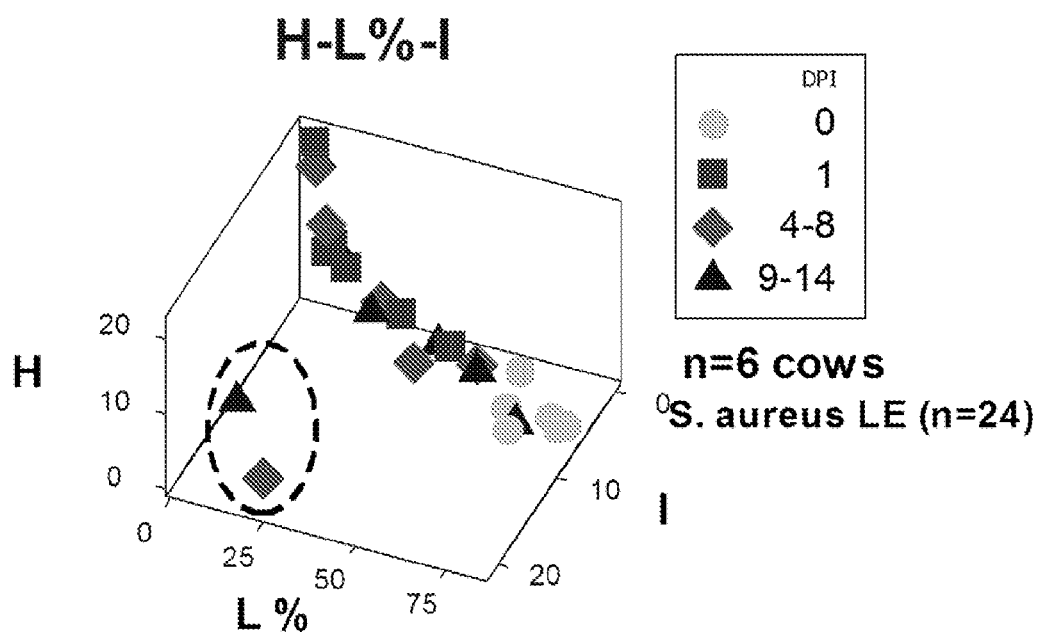
FIGS. 10A-B are graphs showing patterns which facilitate discrimination based on clustering according to one embodiment of the present invention.
Figure 10B:
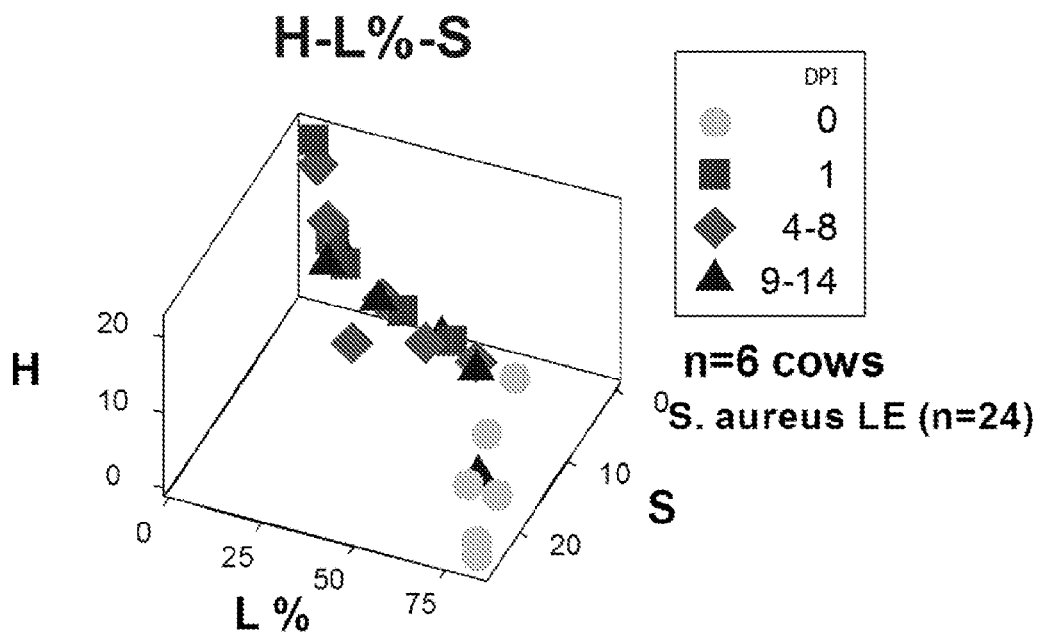

FIG. 10B showed a feature (a perpendicular inflection of a single, one data point-wide line) not predictable or observed in a tabular format. Furthermore, the central feature of the design (no number and/or input variable is critical) was documented: an interaction not measured by the first two steps was, nevertheless, retrieved and its relevance documented. In addition, as shown above, the [SL/M]/[P/L] ratio was detected as an informative data structure, even though it was not measured in the first two steps of this method. Its numerator (the [SL/M] ratio) was not included in any of the three variables measured in FIG. 9A, B.

The [SL/M]/[P/L] ratio—which differed between 0-DPI and later observations-assesses, at least, four levels of complexity: (i) the SL/M interaction, (ii) the P/L interaction, (iii) the interaction resulting from assessing the SL/M and the P/L ratios, and (iv) the overall (higher-level/System-level) interaction resulting from investigating all indicators in a 3D space. The higher value of the [SL/M]/[P/L] ratio in 0 DPI than later observations was only detected by the 3D plot that revealed distinct and informative patterns. The variables actually measured (columns H, I, and S, Table II) did not measure the [SL/M]/[P/L] ratio: column H=P/L (the ratio generated by dividing the percentage of phagocytes [M+PMN] over the L %), column I=[MC/N] (the ratio generated by dividing the MC/N ratio [the percentage of mononuclear cells or MC] over the percentage of polymorphonuclear cells [PMN or N]), and column S=[MC/N]/[P/L] (the ratio generated by dividing the MC/N ratio over the P/L ratio). Thus, none of the variables measured in FIG. 9A or B assessed the SL/M ratio (the percentage of 'small leukocyte' [L+M] over the N %).

Given the major properties of complex systems (novelty, irreducibility, and unpredictability), it is futile to control the leukocyte contents of the new columns (secondary variables) created in the data expansion step (Table II). Hence, this method does not focus on the variables actually measured by 3D plots (the reason why the leukocyte contents of Table II columns are not identified). Instead, this method focuses on the features or properties shown by the patterns generated when secondary variables, alone or together with input variables, are measured in 3D space. Consequently, any data set derived from input data can be used by this method, provided that distinct, non-random, and informative patterns are revealed after the data structuring and expansion steps are conducted. As demonstrated below, new information (i.e., 'novelty') emerges, regardless of the variables actually measured (new information cannot be predicted, but can be observed).

Specifically, in addition to L %, the remaining variables measured in plots FIGS. 9A and 9B were P/L (column H, Table II), MC/N (column I, Table II), and [MC/N]/[P/L] (column S, Table II). While the [SL/M]/[P/L] ratio was demonstrated above to be an informative variable, the numerator of this data combination (SL/M) was not measured by any axis of FIGS. 9A and 9B. Therefore, the identification of secondary (combined) data is irrelevant before data structuring and expansion are conducted. However, identification of distinct and biologically meaningful patterns (such as the perpendicular data inflection that separates healthy (0 DPI) from infected ($\geq 1$ DPI) individuals) allows the retroactive identification of relevant interactions (such as, in this example, the data associated with the complex SL/M]/[P/L] ratio). Thus, an embodiment of this method is that recovery of informative and new (emergent) data structures occurs after pattern recognition is conducted, not before data structuring/expansion is implemented.

Therefore, the composition of each column (columns identified with letters D- . . . T, Table II) is irrelevant by itself. It is shown that a simple ratio (the SL/M) that provided valuable information was not measured in any of the 3 axes evaluated. Hence, the variables actually measured in any plot are not by themselves relevant. New and valuable information may be retrieved, even if not directly or explicitly measured. If, first, many data structures that show some features are created and, at the end, only those that reveal distinct patterns are selected, then any group of 3-D data combinations (derived from the primary data) can be used. That is so because, the 'more complex' the data structure, the more likely an 'emergent'/new information will be revealed. The essence of the method is to allow the creation (and measurement) of very complex structures, e.g., double, triple, quadruple ratios, which are then measured in 3D space. It is then demonstrated that it is not the (input or derived) data actually measured what matters but the observation of 3D data patterns that reveal specific and distinct features.

In contrast, the foundation of this invention is the creation of a one-data point wide, single, line of observations. Such feature, demonstrated (at least under one angle or perspective) in all 3D plots, reduces data variability. Once such line is created, any data point can only fall within such line (data variability is eliminated from all dimensions except such line). Such creation eliminates the use of statistical analyses and numerical cut-off points. While an infinite number of single lines of observations could be created (e.g., the P/L vs. L %, measured in FIG. 9B), the risk of too much information is prevented in step III: only plots revealing distinct data patterns (e.g., perpendicular data inflections) are selected. By using strategies of opposite effects, this method strikes a balance between enhanced information and usability.

The last sub-step of selecting distinct and informative patterns (generation of new information) is documented by FIG. 10A, which distinguished two late (one 4-8 and one 9-14 DPI) observations (oval, FIG. 10A). While receiving a lower priority than FIG. 10B, this method also considers FIG. 10A because it revealed a cluster (oval, FIG. 10A). Secondary data structures can reveal distinct patterns even when the content of some (or all) input variables is unknown. In spite of such an apparent omission, this method can retrieve not only the input values of every observation (and data subset) differentiated but also more variables than investigated. For instance, data on multiple variables can be retrieved even though only 3 axes were investigated.

Figure 11A:
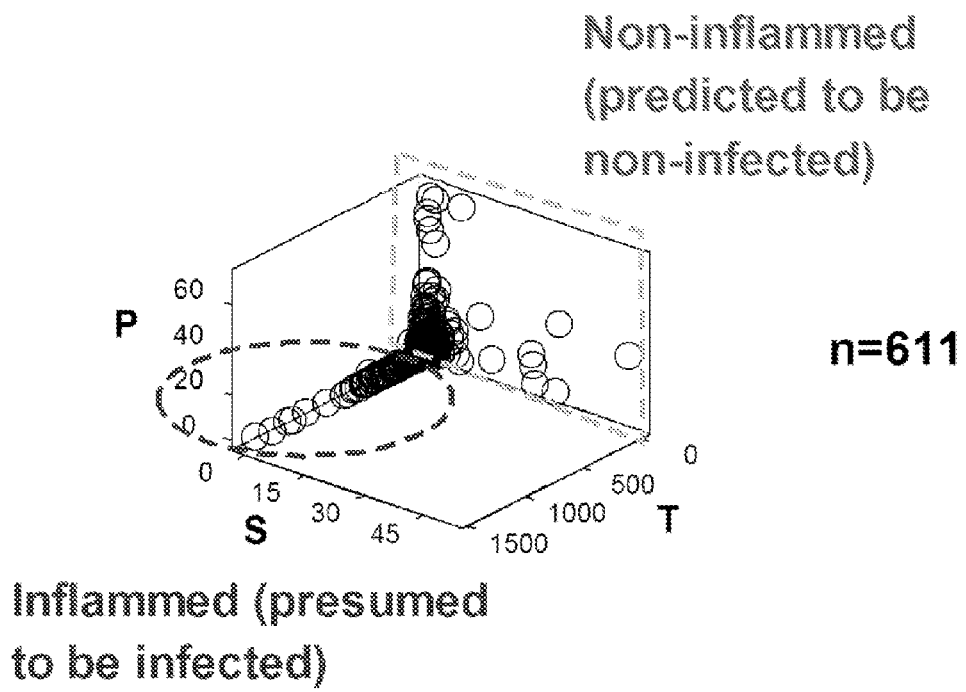
FIGS. 11A-D are graphs showing differentiation between negatives and positives (including the detection of false negatives and positives) according to one embodiment of the present invention.
Figure 11B:
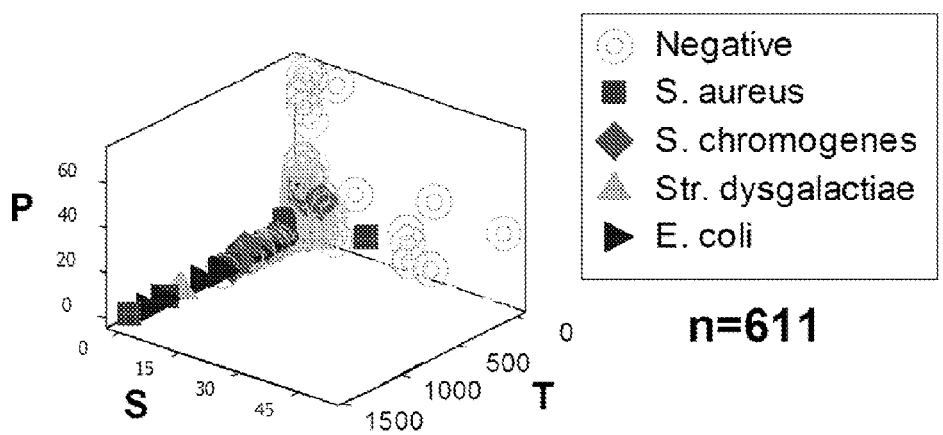
Figure 11C:
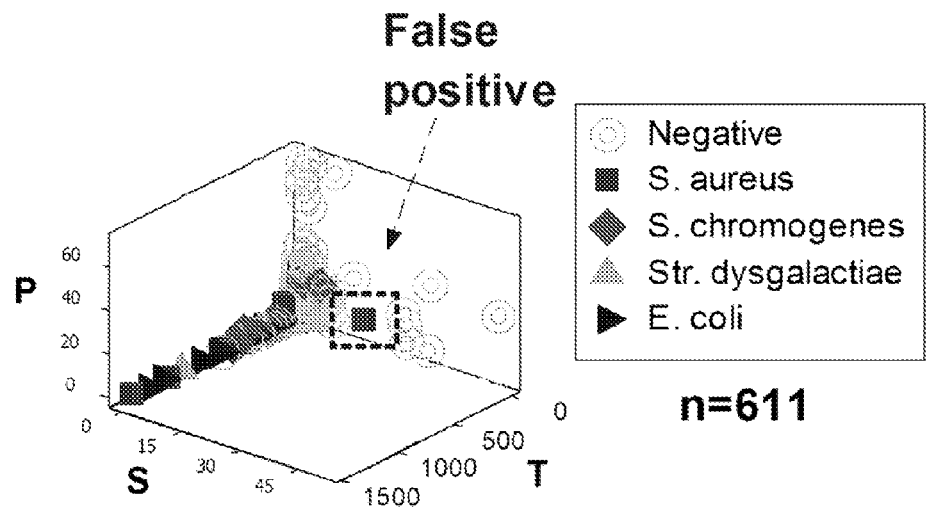
Figure 11D:
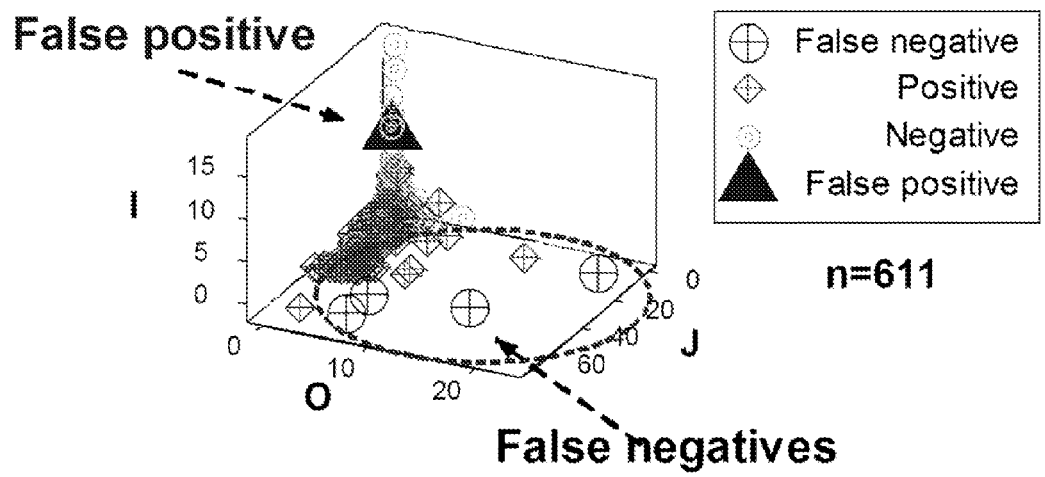

The fourth step is data interpretation, which is performed according to the principles of redundancy, reproducibility, and contrasts. FIGS. 11A-D show differentiation between 'negatives' and 'positives' (including detection of 'false negatives' and 'false positives'). Structures that reveal distinct pattern (e.g., at least one perpendicular data inflection, (predominantly) non-overlapping patterns, and/or contrasts may be used in real-time assessments on inflammation (FIG. 11A), provided that either earlier (from similar datasets) or later (from the same dataset) information on discrete variables become available, such as bacteriological test results (FIG. 11A, B). The detection of 3D inflections act as graphic equivalents of cut-off points, without generating the 'cost of dichotomization, e.g., 'non-infected' and 'infected' observations are perpendicular to one another. Contrasts, such as bacterial-positive observations located within the bacterial-negative subset (FIG. 11C) or bacterial-negative observations located within the bacterial-positive subset may be suspected to be false positive and false negative, respectively. Such interpretations are generated on the basis of empirical data (at least one prior or later microbiological test), distinct patterns, and redundancy (at least two different data structures supporting the same inference, FIGS. 11C, D), not the prior selection of any specific variable or numerical cut-off.

Figure 12A:
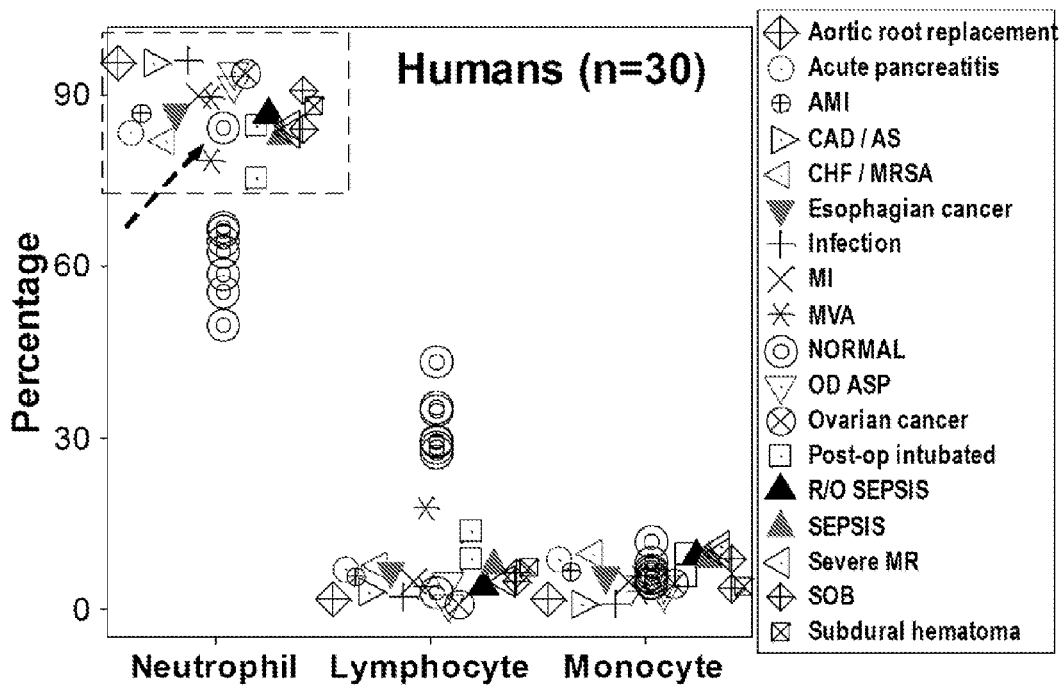
FIG. 12A is a graph showing data collected from both normal humans and humans experiencing medical conditions according to previous methods.
Figure 12B:
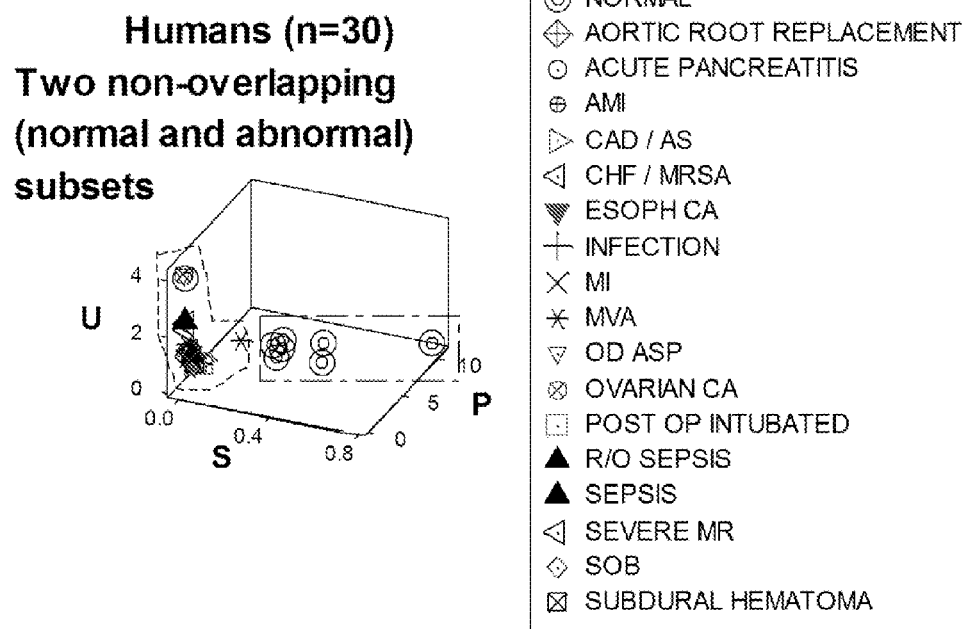
FIGS. 12B-C are graphs showing data collected from both normal humans and humans experiencing medical conditions according to one embodiment of the present invention.
Figure 12C:
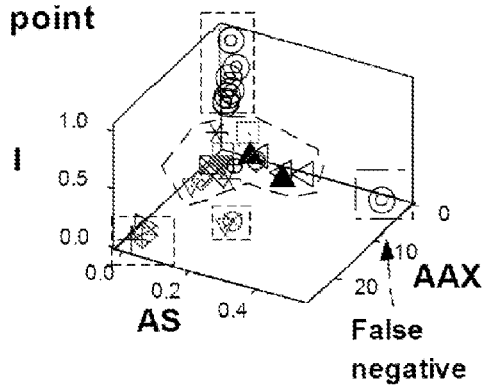
Figure 13:
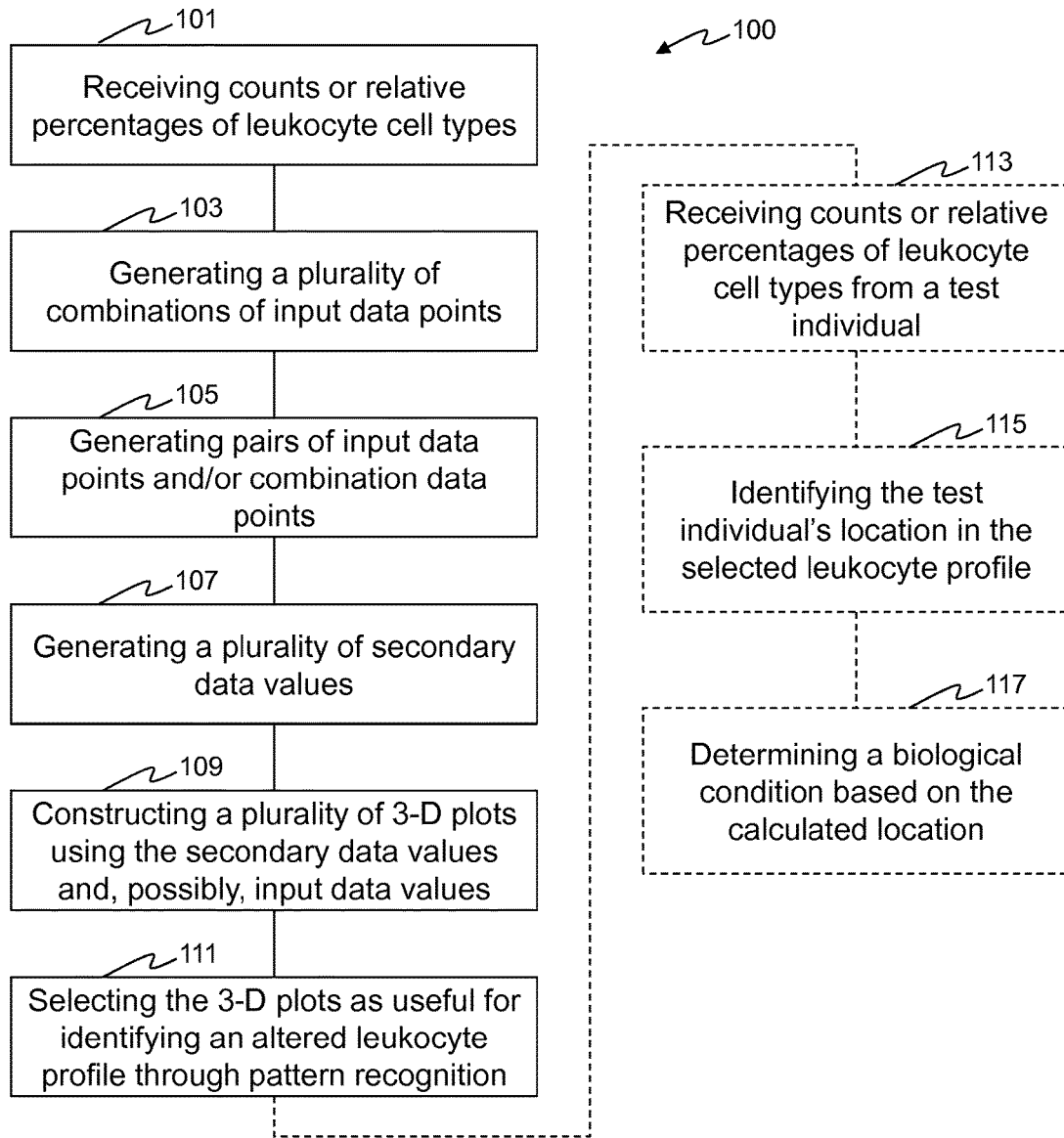
FIG. 13 is a flowchart showing one embodiment of the present invention.

Data collected from both normal humans and humans experiencing 17 medical conditions showed poor discrimination under previously used methods. No medical condition could be distinguished from one another. One individual, regarded to be normal by medical tests, showed leukocyte values within the range of 17 medical conditions (a false negative observation, arrow, FIG. 12A). When the present method is applied, no data overlapping was observed between the normal individuals and all individuals with medical conditions (FIG. 12B). In addition, the combined use of several data structures, generated by this method, differentiated five health-related groups (FIGS. 12B, C). The hypothesis of a false negative observation was also supported (arrow, FIG. 12C). This means that new information can be extracted from the same data even when the conditions assessed are not necessarily associated with infections. While 17 human medical conditions were not distinguished when the classic method was used (rectangle, FIG. 12A) when 3D patterns were assessed and at least one perpendicular data inflection and/or clusters were detected, the use of several (and different) data structures, together, distinguished 5 clusters (the 'normal' subset and 3 groups of medical conditions, in addition to a false-negative observation, FIGS. 12B, C.

One embodiment of the invention can also be described as a pattern recognition-oriented method applied to detect and distinguish immuno-microbial interactions, which measures, at least, leukocyte data, and is performed in three phases: (i) data expansion, (ii) pattern reduction, and (iii) pattern discrimination.

By combining and recombining input data, sets of three variables each are then explored with three-dimensional (3D) plots, i.e., the expression of different patterns is largely augmented. The problem likely to be then generated (an excessive number of patterns, not necessarily informative) is prevented by reducing the number of non-informative patterns (not by reducing data values or variables). Pattern reduction is performed in the second phase, using an objective set of decision rules.

Two or more data structures that convey similar information are utilized to detect and differentiate data subsets. Such strategy expands and compresses the expression of data subsets revealing—without using any numerical cut-off value, i.e., without generating the 'cost of dichotomization' problem—the exact (graphic) cut-off point that results in (partially or totally) non-overlapping data subsets that, in addition to quantitative differences (those expressed by continuous data), also differ in discrete (discontinuous) variables, such as 'non-inflamed' and 'inflamed' classes.

Another embodiment of the invention can be described as a method using the steps of data expansion, pattern reduction, pattern discrimination, and data recovery.

Data expansion is the creation of secondary data combinations, and expression of 3D patterns. Based on inputs (data on counts or relative percentages of leukocytes, such as lymphocytes [L], macrophages/monocytes [M], and polymorphonuclear cells or neutrophils [PMN or N]), secondary data combinations are created. The combinations may include any data combination includes data from, at least, two of the cell types investigated. The combinations may also include any pair of such combinations that includes all data points of all cell types. The combinations may also include any pair of such combinations that includes, at least, one ratio (i.e., the percentage of one variable over the percentage of another variable, whether input or secondary).

Ratios can be simple (both the numerator and the denominator include data on a single cell type, e.g., the L/M ratio) or complex (two or more cell types are measured by the numerator, the denominator), or both. For example, one complex ratio is the overall ratio created by dividing the L/M ratio over the N/L ratio, (i.e., the [L/M]/[N/L]).

At least three pairs of variables so created will reveal a single, one data point-wide line of data points. Input and/or secondary data combinations are grouped in sets of three variables each, and explored in three-dimensional (3D) plots.

The step of pattern reduction comprises rules for selection of distinct 3D patterns. Distinct 3D patterns include perpendicular data inflections, data bifurcations, non-overlapping data clusters, or combinations of the above. 3D plots not showing distinct patterns are discarded. Distinct patterns are selected according to priority. Highest priority is at least a triple perpendicular data inflection (3 data subsets, perpendicular to one another, i.e., data points that occupy 3 planes). Next highest is at least one perpendicular data inflection. Next highest is data bifurcations. Next highest is non-overlapping data clusters.

The step of pattern discrimination determines cut-offs and data recovery. Cut-offs means using different data structures that convey similar information but compress or expand the expression of particular data points or subsets. In this way, non-overlapping subsets are distinguished (e.g., 'non-inflamed' vs. 'inflamed' subsets). Data recovery is based on distinct graphic patterns and/or discrete data patterns, the numerical values of data points or subsets so distinguished are extracted, using input and/or combination data.

The invention is at least partially implemented through computer software. The results generated can be used in real-time detection of distinct and/or non-overlapping subsets. In some embodiments, all of the steps of the method are performed through computer software. For example, the computer software receives counts or relative percentages of leukocyte cell types through an input module. The input module may communicate directly with a pathology device (such as a flow cytometer) or may receive the counts or relative percentages manually (e.g., inputted by a human or uploaded as a file into the program). The program, using a processor, generates a plurality of combinations of input data points to provide combination data points. The program, using a processor then generates pairs of i) two input data points, ii) an input data point and a combination data point, or iii) two combination data points. The pairs and combination data points may be stored in memory (such as read-only memory, a database, a hard drive, etc.). The program, using a processor, then generates a plurality of secondary data values from the generated pairs. The program, using the processor constructs a plurality of 3-D plots. The processor may show the 3-D plots on a display in communication with the processor. The 3-D plots may be saved in memory for future access. The processor selects 3-D plots as useful for identifying an altered leukocyte profile through pattern recognition of perpendicular data inflection, data bifurcation, non-overlapping data clusters, or combinations thereof.

There are other potential applications for the present invention. For example, detection of data points suspected to be false, e. g, a data point assigned to a particular discrete class (e.g., 'negative') but located within the range of points assigned with a different discrete class (such as 'positives'). Another application includes differentiation of disease stages (e.g., 'early' vs. 'late' stage). Another application includes differentiation of non-inflamed sub-categories (e.g. 'neither inflamed nor recovered' and 'previously inflamed, now recovered'). Another application includes differentiation between individuals regarded to be 'fast', 'average', or 'slow' immune responders. Another application includes differentiation of medical conditions, even when infection is not suspected.

Although the present invention has been described with respect to one or more particular embodiments, it will be understood that other embodiments of the present invention may be made without departing from the spirit and scope of the present invention. Hence, the present invention is deemed limited only by the appended claims and the reasonable interpretation thereof.

What is claimed is:

1. A method for identifying an altered leukocyte profile by pattern recognition comprising the steps of:
    a) receiving, at an input module executable on a processor, counts or relative percentages of more than two leukocyte cell types in a biological fluid from each of one or more individuals, said counts or percentages constituting input data points;
    b) generating, using the processor, a plurality of combination data points, each combination data point being a value calculated from more than two input data points, each input data point corresponding to a distinct leukocyte cell type;
    c) generating, using a processor, pairs of i) an input data point and a combination data point or ii) two combination data points;
    d) generating, using a processor, a plurality of secondary data values from the pairs generated in c);
    e) constructing, using a processor, a plurality of 3-D plots, each plot having a plurality of plot points, each plot point having three coordinates, wherein each coordinate is an input data point or a secondary data value, and at least one of the coordinates is a secondary data value; and
    f) performing, using the processor, pattern recognition of: perpendicular subsets of the plot points, a bifurcated subset of the plot points, two or more non-overlapping subsets of the plot points, or combinations thereof, thereby selecting the 3-D plots useful for identifying an altered leukocyte profile.

2. The method of claim 1, wherein the secondary data values comprise complex ratios of input data points, wherein a numerator or a denominator of the complex ratios of input data points contains input data points from two or more leukocyte cell types.

3. The method of claim 2, wherein the denominator of the complex ratios of input data points contain input data points from two or more leukocyte cell types.

4. The method of claim 2, wherein the numerator of the complex ratios of input data points contain input data points from two or more leukocyte cell types.

5. The method of claim 2, wherein each of the leukocyte cell types comprise lymphocytes, monocytes, basophils, eosinophils, or neutrophils.

6. The method of claim 5, wherein at least one of the complex ratios is $(M/N)/(N/L)$, wherein M represents a count or relative percentage of monocytes, N represents a count or relative percentage of neutrophils, and L represents a count or relative percentage of lymphocytes.

7. The method of claim 5, wherein the complex ratio is $[(M*L)/N]/(P/L)$, wherein M represents a count or relative percentage of monocytes, N represents a count or relative percentage of neutrophils, L represents a count or relative percentage of lymphocytes, and P represents a count or relative percentage of the combination of monocytes and neutrophils.

8. The method of claim 1, wherein the input data points represent counts or percentages over multiple times.

9. The method of claim 8, wherein the input data points over multiple times are received from a single individual.

10. The method of claim 1, wherein the biological fluid is blood, milk, or peritoneal fluid.

11. The method of claim 1, further comprising the steps of:
    receiving counts or relative percentages of leukocyte cell types in a second biological fluid from a test individual;
    calculating a test individual's location in a selected leukocyte profile; and
    determining a biological condition based on the calculated location.

12. The method of claim 1, wherein performing pattern recognition comprises determining differences in: spatial location between data points, data points projected on different planes, or data points projected on different dimensions.

13. The method of claim 1, further comprising displaying, on a display in communication with the processor, the plurality of 3-D plots.

14. The method of claim 1, further comprising displaying, on a display in communication with the processor, the plurality of 3-D plots for identifying an altered leukocyte profile.

15. The method of claim 1, wherein the input module is a user interface comprising a human input device, wherein the human input device is configured to receive counts or relative percentages of at least two leukocyte cell types in a biological fluid of at least one individual manually.

16. The method of claim 1, wherein the input module is configured to communicate electronically with a pathology device.

17. The method of claim 1, further comprising storing the pairs generated in c) in a non-transitory computer-readable storage medium.

18. The method according to claim 1, further comprising storing the 3-D plots constructed in e) in a non-transitory computer-readable storage medium.

* * * * *